(12) United States Patent
Garcia-Bengochea et al.

(10) Patent No.: US 12,239,307 B2
(45) Date of Patent: Mar. 4, 2025

(54) MODULAR LENGTH ADJUSTABLE TUBULAR RETRACTOR AND A TUBE BREAKER

(71) Applicant: JGMG BENGOCHEA, LLC, Jacksonville, FL (US)

(72) Inventors: Javier Garcia-Bengochea, Jacksonville, FL (US); John Souza, Sr., Monroe, NC (US)

(73) Assignee: JGMG BENGOCHEA, LLC, Jacksonville, FL (US)

( * ) Notice: Subject to any disclaimer, the term of this patent is extended or adjusted under 35 U.S.C. 154(b) by 0 days.

(21) Appl. No.: 18/515,163

(22) Filed: Nov. 20, 2023

(65) Prior Publication Data

US 2024/0277328 A1 Aug. 22, 2024

Related U.S. Application Data

(60) Provisional application No. 63/447,072, filed on Feb. 21, 2023.

(51) Int. Cl.
*A61B 17/02* (2006.01)
*A61B 17/34* (2006.01)
*A61B 90/00* (2016.01)

(52) U.S. Cl.
CPC .. *A61B 17/0293* (2013.01); *A61B 2017/3443* (2013.01); *A61B 2090/037* (2016.02)

(58) Field of Classification Search
CPC ... A61B 17/02; A61B 17/0206; A61B 17/025; A61B 17/0256; A61B 17/0218
See application file for complete search history.

(56) References Cited

U.S. PATENT DOCUMENTS

| 5,318,542 | A | * | 6/1994 | Hirsch | A61M 25/065 604/164.11 |
|---|---|---|---|---|---|
| 2019/0343504 | A1 | * | 11/2019 | Beger | A61B 17/0218 |
| 2020/0360048 | A1 | * | 11/2020 | White | A61B 1/00045 |
| 2022/0313238 | A1 | * | 10/2022 | Garcia-Bengochea | A61B 17/0293 |

\* cited by examiner

*Primary Examiner* — Christopher J Beccia
(74) *Attorney, Agent, or Firm* — McNees Wallace & Nurick LLC

(57) ABSTRACT

A disposable or reusable length adjustable tubular retractor, a surgical system, and a tube breaker for adjusting the length of the length adjustable tubular retractor are provided. The length adjustable tubular retractor includes a cylindrical body and at least one or a plurality of grooves or through slots or a combination thereof circumferentially disposed along the cylindrical body at predetermined positions. Each of the at least one or a plurality of grooves, through slots, or a combination thereof is configured such that the cylindrical body is breakable at each of the predetermined positions to form a size-selected length adjustable tubular retractor. A surgical system includes the length adjustable tubular retractor and a retractor handle.

21 Claims, 24 Drawing Sheets

MODULAR LENGTH ADJUSTABLE TUBULAR RETRACTOR AND A TUBE BREAKER

CROSS-REFERENCE TO RELATED APPLICATIONS

This application claims the benefit of U.S. Provisional Patent Application Ser. No. 63/447,072, filed on Feb. 21, 2023, the content of which is incorporated herein by reference in its entirety.

FIELD OF THE INVENTION

The present application provides in various embodiments, exemplary devices, systems, and methods for providing selectable sized surgical retractors for facilitating access to a surgical site within the body, particularly the spine.

SUMMARY

In various embodiments, the disclosure provides a disposable or reusable length adjustable tubular retractor that is scored and/or through slotted to enable breakage of the retractor at one or more locations along a length. Accordingly, the length adjustable tubular retractor includes a cylindrical body having a hollow interior, a central axis, proximal end and distal ends and internal and exterior surfaces, where one or both of the internal surface and the exterior surface of the cylindrical body includes at least one or a plurality of grooves (scores), or through slots, or a combination thereof, circumferentially disposed along the length of the cylindrical body at predetermined positions, the at least one or plurality of the grooves or through slots positioned along the cylindrical body between the proximal end and the distal end, wherein each of the at least one or a plurality of grooves, through slots or a combination thereof is configured such that the cylindrical body is breakable at each of the predetermined positions to form a size-selected length adjustable tubular retractor.

In an embodiment, a length adjustable tubular retractor includes a scored tubular retractor including a cylindrical body, the scored tubular retractor being adapted for breaking away at least a portion of the cylindrical body to thereby adjust the length of the tubular retractor. The cylindrical body has a proximal end, a distal end, an internal surface, and an exterior surface. The internal surface faces toward a central axis of the cylindrical body, and the exterior surface faces away from the central axis of the cylindrical body. The cylindrical body includes at least one exterior groove disposed circumferentially within the exterior surface of the cylindrical body between the proximal end and the distal end. The at least one exterior groove is disposed at a predetermined position along the central axis from the proximal end to the distal end.

In some embodiments, the at least one exterior groove includes a V-shape, the V-shape having an angle at its apex along the exterior surface.

In some embodiments, the at least one exterior groove includes a U-shape, the U-shape having a curvature along the exterior surface.

In some embodiments, the length adjustable tubular retractor includes a plurality of exterior grooves spaced apart along the length of the cylindrical body between the proximal end and the distal end.

In some embodiments, the length adjustable tubular retractor includes at least one through slot circumferentially disposed through the cylindrical body between the proximal end and the distal end.

In some embodiments, the length adjustable tubular retractor includes at least one through slot circumferentially disposed through the cylindrical body between the proximal end and the distal end and along a portion of the at least one exterior groove.

In some embodiments, the length adjustable tubular retractor includes a plurality of exterior grooves spaced apart along the length of the cylindrical body between the proximal end and the distal end, and a plurality of through slots, each exterior groove comprising at least one of the plurality of through slots disposed along a portion of the exterior groove.

In some embodiments, the length adjustable tubular retractor includes a plurality of exterior grooves spaced apart along the length of the cylindrical body between the proximal end and the distal end, and a plurality of through slots, each exterior groove comprising at least one of the plurality of through slots disposed along a portion of the exterior groove, and the plurality of through slots is disposed in a staggered arrangement along the length of the cylindrical body between the proximal end and the distal end.

In some embodiments, the length adjustable tubular retractor includes a plurality of exterior grooves spaced apart along the length of the cylindrical body between the proximal end and the distal end, and a plurality of through slots, each exterior groove comprising at least one of the plurality of through slots disposed along a portion of the exterior groove, and the plurality of through slots is disposed in a spiral arrangement along the length of the cylindrical body between the proximal end and the distal end.

In some embodiments, the length adjustable tubular retractor includes a plurality of exterior grooves spaced apart along the length of the cylindrical body between the proximal end and the distal end, and a plurality of through slots, each exterior groove comprising at least one of the plurality of through slots disposed along a portion of the exterior groove, and each of the plurality of through slots is disposed sequentially along the length of the cylindrical body between the proximal end and the distal end at 90 degrees from each adjacent through slot.

In some embodiments, the length adjustable tubular retractor includes at least one interior groove disposed circumferentially within the internal surface of the cylindrical body, and the at least one interior groove is aligned with and opposite the at least one exterior groove.

In some embodiments, the length adjustable tubular retractor includes a retractor handle extending from the proximal end of the cylindrical body.

In some embodiments, the length adjustable tubular retractor includes a retractor handle extending from the proximal end of the cylindrical body and further includes a frame extending from the retractor handle. The frame has two generally planar arms facing one another and configured to retain one or more attachments extending into the cylindrical body.

In some embodiments, the length adjustable tubular retractor includes a retractor handle extending from the proximal end of the cylindrical body and further includes a frame extending from the retractor handle. The frame has two generally planar arms facing one another and configured to retain one or more attachments extending into the cylindrical body, and two generally planar arms facing one another are configured to retain one or more of lighting and suction attachments.

In an embodiment, a length adjustable tubular retractor includes a scored tubular retractor comprising a cylindrical body, at least one exterior groove and one interior groove, and at least one through slot positioned between the proximal end and the distal end of the cylindrical body. The at least one interior groove is aligned with and opposite the at least one exterior groove, and the at least one through slot is circumferentially disposed through the cylindrical body along a portion of the aligned exterior and interior groove.

In an embodiment, a method for providing a size-selected length adjustable tubular retractor includes (i) providing a length adjustable tubular retractor; (ii) selecting one of the predetermined positions along the cylindrical body at which to break the retractor; and (iii) engaging a tool to enable a break at the selected predetermined position at the groove located at the selected predetermined position. The length adjustable tubular retractor includes a scored tubular retractor including a cylindrical body, the scored tubular retractor adapted for breaking away at least a portion of the cylindrical body to thereby adjust the length of the tubular retractor, the cylindrical body having a proximal end, a distal end, an internal surface, and an exterior surface, the internal surface facing toward a central axis of the cylindrical body, the exterior surface facing away from the central axis of the cylindrical body, the cylindrical body including at least one exterior groove disposed circumferentially within the exterior surface of the cylindrical body between the proximal end and the distal end. The at least one exterior groove is disposed at a predetermined position along the central axis from the proximal end to the distal end.

In some embodiments, the tool is a pair of human hands, one hand disposed proximal to the selected predetermined position and the other hand is disposed distal to the selected predetermined position, each hand gripping the retractor along the central axis. The action of breaking is accomplished by rotation of the hands off of the central axis to break the cylindrical body.

In some embodiments, the tool is a pair of opposable insertion rods, clamps, or a combination thereof, one of which is engaged with the cylindrical body disposed proximal to the selected predetermined position and the other of which is engaged with the cylindrical body distal to the selected predetermined position, each of the pair of opposable insertion rods, clamps, or a combination thereof engaging the retractor along the central axis. The action of breaking is accomplished by rotation of the pair of opposable insertion rods, clamps, or a combination thereof off of the central axis to break the cylindrical body.

In an embodiment, a length adjustable tubular retractor system includes a length adjustable tubular retractor and a tube breaker for adjusting the length of the length adjustable tubular retractor. The length adjustable tubular retractor includes a scored tubular retractor including a cylindrical body, the scored tubular retractor adapted for breaking away at least a portion of the cylindrical body to thereby adjust the length of the tubular retractor, the cylindrical body having a proximal end, a distal end, an internal surface, and an exterior surface, the internal surface facing toward a central axis of the cylindrical body, the exterior surface facing away from the central axis of the cylindrical body, the cylindrical body including at least one exterior groove disposed circumferentially within the exterior surface of the cylindrical body between the proximal end and the distal end. The at least one exterior groove is disposed at a predetermined position along the central axis from the proximal end to the distal end. The tube breaker includes a protuberance portion, the protuberance portion having a top, side, and bottom, the side of the protuberance portion disposed between the top and bottom of the protuberance portion, the protuberance portion extending from the top toward the bottom along a longitudinal axis, the protuberance portion having cross-sectional areas along the longitudinal axis; an upper portion, the upper portion having a generally cylindrical shape, the upper portion adapted to be slidably inserted in a length adjustable tubular retractor, the upper portion having a first end, the upper portion extending from the first end along the longitudinal axis toward the protuberance portion and connecting to the top of the protuberance portion, the upper portion having cross-sectional areas along the longitudinal axis, wherein the cross-sectional area at the top of the protuberance portion is greater than the cross-sectional area of the upper portion where the upper portion connects to the top of the protuberance; a lower portion, the lower portion having a generally cylindrical shape, the lower portion adapted to be slidably inserted in a length adjustable tubular retractor, the lower portion having a second end, the lower portion extending from the second end along the longitudinal axis toward the protuberance portion and connecting to the bottom of the protuberance portion, the lower portion having cross-sectional areas along the longitudinal axis, wherein the cross-sectional area at the bottom of the protuberance portion is greater than the cross-sectional area of the lower portion where the lower portion connects to the bottom of the protuberance portion; and a plurality of marks disposed on the upper portion, protuberance portion, and lower portion, each mark indicating a relative longitudinal location measured from the first end. The upper portion and lower portion are configured to enable a break, when inserted in a length adjustable tubular retractor, at a selected predetermined position on the length adjustable tubular retractor by an action of breaking, wherein the action of breaking is accomplished by hands of the operator gripping the length adjustable tubular retractor and tube breaker and applying force or moment to induce bending moment greater than the bending moment the selected predetermined position on the length adjustable tubular retractor can withstand.

In some embodiments, the upper portion of the tube breaker is chamfered at the first end such that the cross-sectional areas are decreasing along the longitudinal axis toward the first end.

In some embodiments, the lower portion of the tube breaker is chamfered at the second end such that the cross-sectional areas are decreasing along the longitudinal axis toward the second end.

In some embodiments, each mark of the tube breaker is spaced equidistance of approximately 5-15 mm.

In some embodiments, each mark of the tube breaker is spaced equidistance of approximately 10 mm.

Figure 1:
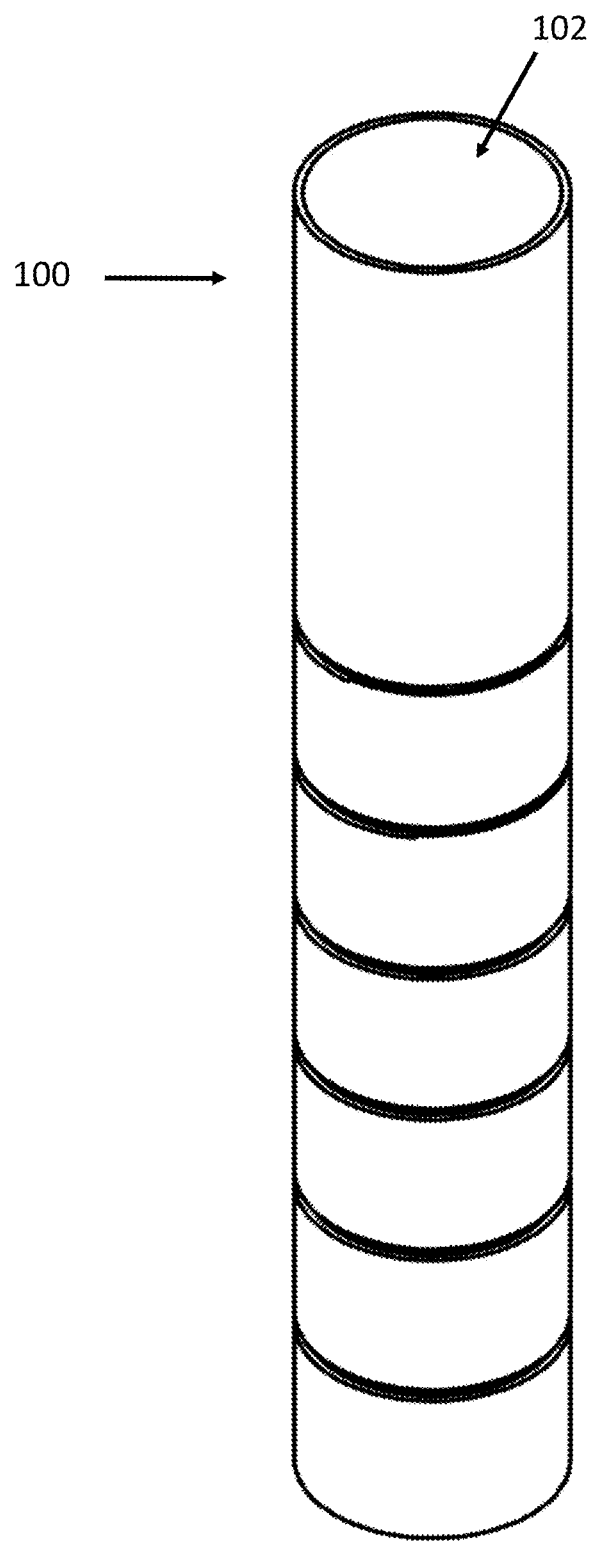
FIG. 1 is an upper perspective view showing an exemplary length adjustable tubular retractor.

Other features and advantages of the present invention will be apparent from the following more detailed description, taken in conjunction with the accompanying drawings, which illustrate, by way of example, the principles of the invention.

Additional embodiments will now be described employing reference numerals to identify the features of the length adjustable tubular retractor.

TABLE OF REFERENCE NUMERALS
The following Reference Numeral Key describes various features as shown in the drawings and relating to the various embodiments as set forth in the description and claims:

| Description | Num | Description | Num |
|---|---|---|---|
| Disposable Length adjustable tubular Retractor | 100 | Hollow Interior | 102 |
| Size-selected Disposable Length adjustable tubular Retractor | 101 | Surgical System | 103 |
| Cylindrical body | 10 | Through slot | 40 |
| Proximal End | 11 | Angle | 42 |
| Distal End | 12 | Proximal Edge | 43 |
| Internal Surface | 13 | Distal Edge | 44 |
| Exterior Surface | 14 | First Taper Angle | 45 |
| Central Axis | 15 | Second Taper Angle | 46 |
| Cross Section | 16 | Through slot End | 48 |
| Distance, Equidistance, Non-equidistance | 17 | Through slot Edge | 49 |
| V-shape | 18 | Mounting Bracket | 50 |
| U-Shape | 19 | Plate | 51 |
| Exterior Groove/Groove | 20 | First Arm | 59 |
| Predetermined Position | 21 | Second Arm | 60 |
| Angle | 22 | Device Emplacement | 62 |
| Apex | 23 | Surgical Tool | 63 |
| Interior Groove | 25 | Through slot Edge Angle | 64 |
| Right Angle | 27 | Circumference | 66 |
| Retractor Arm | 30 | Residual Area | 67 |
| Retractor Handle | 31 | Lost Area | 68 |
| Ring | 32 | Residual Thickness | 70 |
| Arm | 34 | Predetermined Thickness | 71 |
| Frame | 35 | Depth | 72 |
| Two Generally Planar Arms | 36 | | |
| Tube Breaker | 200 | Upper Portion | 211 |
| Protuberance Portion | 201 | First End | 212 |
| Top (Protuberance Portion) | 202 | Cross-Sectional Areas (Upper Portion) | 213 |
| Side (Protuberance Portion) | 203 | Cross-Sectional Area (Where the Upper Portion Connects to the Top of the Protuberance) | 214 |
| Bottom (Protuberance Portion) | 204 | Lower Portion | 215 |
| Longitudinal Axis | 205 | Second End | 216 |
| Cross-Sectional Areas (Protuberance Portion) | 206 | Cross-Sectional Areas (Lower Portion) | 217 |
| Cross-Sectional Area (At the Top of the Protuberance Portion) | 207 | Cross-Sectional Area (Where the Lower Portion Connects to the Bottom of the Protuberance) | 218 |
| Cross-Sectional Area (At the Bottom of the Protuberance Portion) | 208 | Recess | 219 |
| Mark | 209 | Selected Predetermined Position | 220 |

DETAILED DESCRIPTION

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

Shortcomings in the art have been overcome by the instant invention which provides a device, system and methods that ensure efficient selectable provision in the surgical suite of an optimally sized tubular retractor that meets the specifications for access to the anatomical site of interest, for example the spine, of a patient. In some specific embodiments, the invention provides a length adjustable tubular retractor that may be selectably sized in the surgical suite to fit a particular patient. In some further embodiments, the length adjustable tubular retractor may incorporate features to minimize obstructions in the surgical field and provides a variety of options for affixing one or a combination of fluid movement and light sources that are low profile and occupy only nominal space within the tubular retractor. While reference herein is made to some specific embodiments of the length adjustable tubular retractor that are disposable, and thus, single use, in other possible embodiments the length adjustable tubular retractor may be multi-use and re-sterilizable. As such, the term "disposable" is used only in reference to representative embodiments and is not limiting.

In various embodiments, the disclosure provides a disposable or reusable, length adjustable tubular retractor that is scored and/or through slotted to enable breakage of the retractor at one or more locations along a length. Accordingly, the length adjustable tubular retractor includes a cylindrical body having a hollow interior, a central axis, proximal end and distal ends and internal and exterior surfaces, where one or both of the internal surface and the exterior surfaces of the cylindrical body includes at least one or a plurality of grooves (scores) or through slots or a combination thereof circumferentially disposed along the cylindrical body at predetermined positions, the at least one or plurality of the grooves or through slots positioned along the cylindrical body between the proximal end and the distal end, wherein each of the at least one or a plurality of grooves, through slots or a combination thereof is configured such that the cylindrical body is breakable at each of the predetermined positions to form a size-selected length adjustable tubular retractor.

In some embodiments, the disposable length adjustable tubular retractor is disposable. In other embodiments, the disposable length adjustable tubular retractor is reusable. In some embodiments, the length adjustable tubular retractor includes only one groove or only one through slot. In some embodiments, the length adjustable tubular retractor includes a plurality of grooves or a plurality of through slots.

In some embodiments, the length adjustable tubular retractor includes a plurality of features arranged along the body of the length adjustable tubular retractor, each feature comprising a combination of a groove and a through slot, as more specifically disclosed herein. According to such embodiments, each such feature confers a through slotted opening through the exterior and internal surfaces and into the hollow interior of the length adjustable tubular retractor wherein the through slot is adjacent a groove. According to some such embodiments, the through slot portion of the feature may represent from about 10% to about 90% of the circumference of the length adjustable tubular retractor and the groove portion of the feature may represent from about 10% to about 90% of the circumference of the length adjustable tubular retractor, wherein the sum of the through slot and the groove portions is equal to 100%. In one exemplary embodiment, the through slot portion of the feature may represent about 70% of the circumference of the body of the length adjustable tubular retractor, and the groove portion of the feature may represent about 30% of the circumference of the body of the length adjustable tubular retractor.

In various embodiments, each groove has a shape and a depth (i.e., the distance from the outer surface penetrating the body of the retractor) that is suitable based on the material from which the length adjustable tubular retractor is formed to enable breakage and removal of the portion of the body of the length adjustable tubular retractor below the through slot/groove feature that is broken. In some embodiments, the depth of the groove may be represented in metric units and in other embodiments the depth of the groove may be represented as residual material.

In some embodiments, a length adjustable tubular retractor includes groove features on each of the internal and exterior surfaces of the body of the length adjustable tubular retractor.

Referring now to the drawings, FIG. 1 shows an upper perspective view showing an exemplary length adjustable tubular retractor. The length adjustable tubular retractor 100 includes a cylindrical body having a hollow interior 102.

In some embodiments, a disposable length adjustable tubular retractor 100 includes a cylindrical body 10 having a proximal end 11, distal end 12, internal surface 13, and exterior surface 14, the internal surface 13 facing toward a central axis 15 of the cylindrical body 10, the exterior surface 14 facing away from the central axis 15 of the cylindrical body 10, wherein the cylindrical body 10 has cross sections 16 along the central axis 15; and at least one exterior groove 20 circumferentially disposed along the exterior surface 14 of the cylindrical body 10 between the proximal end 11 and the distal end 12, the at least one exterior groove 20 disposed at a predetermined position 21 along the central axis 15 from the proximal end 11 to the distal end 12, wherein the at least one exterior groove 20 is configured such that the cylindrical body 10 is breakable at each of the predetermined positions 21 to form a size-selected disposable length adjustable tubular retractor 101.

In another embodiment, a disposable length adjustable tubular retractor 100 includes a cylindrical body 10 having a proximal end 11, distal end 12, internal surface 13, and exterior surface 14, the internal surface 13 facing toward a central axis 15 of the cylindrical body 10, the exterior surface 14 facing away from the central axis 15 of the cylindrical body 10, wherein the cylindrical body 10 has cross sections 16 along the central axis 15; at least one exterior groove 20 circumferentially disposed along the exterior surface 14 of the cylindrical body 10 between the proximal end 11 and the distal end 12, the at least one exterior groove 20 disposed at a predetermined position 21 along the central axis 15 from the proximal end 11 to the distal end 12, wherein the at least one exterior groove 20 is configured such that the cylindrical body 10 is breakable at each of the predetermined positions 21 to form a size-selected disposable length adjustable tubular retractor 101; and at least one of through slot 40 circumferentially disposed along the cylindrical body 10 between the proximal end 11 and the distal end 12, the at least one through slot 40 disposed at a predetermined position 21 along the central axis 15, wherein the at least one through slot 40 is configured such that the cylindrical body 10 is disconnected along and at each of the at least one through slot 40 and breakable at each of the predetermined positions 21 to form a size-selected disposable length adjustable tubular retractor 101.

In another embodiment, a disposable length adjustable tubular retractor 100 includes a cylindrical body 10 having a proximal end 11, distal end 12, internal surface 13, and exterior surface 14, the internal surface 13 facing toward a central axis 15 of the cylindrical body 10, the exterior surface 14 facing away from the central axis 15 of the cylindrical body 10, wherein the cylindrical body 10 has cross sections 16 along the central axis 15; and at least one of through slot 40 circumferentially disposed along the cylindrical body 10 between the proximal end 11 and the distal end 12, the at least one through slot 40 disposed at a predetermined position 21 along the central axis 15, wherein the at least one through slot 40 is configured such that the cylindrical body 10 is disconnected along and at each of the at least one through slot 40 and breakable at each of the predetermined positions 21 to form a size-selected disposable length adjustable tubular retractor 101.

In another embodiment, a disposable length adjustable tubular retractor 100 may further include a retractor handle 31, the retractor handle 31 comprising a ring 32 configured to be attached to the disposable length adjustable tubular retractor 100, the ring 32 formed directly onto the disposable length adjustable tubular retractor 100 such that the ring 32 is fixedly attached to the disposable length adjustable tubular retractor 100, and an arm 34 extending from the ring 32.

In another embodiment, a disposable length adjustable tubular retractor 100 may further include a frame 35 extending from a retractor handle 31, the frame 35 having two generally planar arms 36, the two generally planar arms 36 facing one another, the two generally planar arms 36 configured to be attached to a table arm, wherein the frame 35 is configured to receive a cylindrical fastening device such that the cylindrical fastening device clamps the frame 35 and fix the disposable length adjustable tubular retractor 100 thereby when the cylindrical fastening device engages in a fastening mode.

In another embodiment, a surgical system 103 includes a disposable length adjustable tubular retractor 100; a retractor handle 31, including: a ring 32 configured to be attached to the disposable length adjustable tubular retractor 100, the ring 32 formed directly onto the disposable length adjustable tubular retractor 100 such that the ring is fixedly attached to the tubular retractor; and an arm 34 extending from the ring 32; and a mounting bracket 50, including: a plate 51; first and second arms 59, 60 adjacent to and extending from the of the plate 51, the first and second arms 59, 60 each including at least one device emplacement 62 disposed adjacent to the plate 51 to receive and hold in-place a surgical tool 63 at a fixed position and orientation.

In another embodiment, a surgical system may further include a frame 35 extending from a retractor handle 31, the frame 35 having two generally planar arms 36, the two generally planar arms 36 facing one another, the two generally planar arms 36 configured to be attached to a table arm, wherein the frame 35 is configured to receive a cylindrical fastening device such that the cylindrical fastening device clamps the frame 35 and fix the disposable length adjustable tubular retractor 100 thereby when the cylindrical fastening device engages in a fastening mode.

In another embodiment, a tube breaker 200 for adjusting the length of a length adjustable tubular retractor 100, the tube breaker 200 includes a protuberance portion 201, the protuberance portion 201 having a top 202, side 203, and bottom 204, the side 203 of the protuberance portion 201 disposed between the top 202 and bottom 204 of the protuberance portion 201, the protuberance portion 201 extending from the top 202 toward the bottom 204 along a longitudinal axis 205, the protuberance portion 201 having cross-sectional areas 206 along the longitudinal axis 205; an upper portion 211, the upper portion 211 having a generally cylindrical shape, the upper portion 211 adapted to be slidably inserted in a length adjustable tubular retractor 100, the upper portion 211 having a first end 212, the upper portion 211 extending from the first end 212 along the longitudinal axis 205 toward the protuberance portion 201 and connecting to the top 202 of the protuberance portion 201, the upper portion 211 having cross-sectional areas 213 along the longitudinal axis 205, wherein the cross-sectional area 207 at the top 202 of the protuberance portion 201 is greater than the cross-sectional area 214 of the upper portion 211 where the upper portion 211 connects to the top 202 of the protuberance 201; a lower portion 215, the lower portion 215 having a generally cylindrical shape, the lower portion 215 adapted to be slidably inserted in a length adjustable tubular retractor 100, the lower portion 215 having a second end 216, the lower portion 215 extending from the second end 215 along the longitudinal axis 205 toward the protuberance portion 201 and connecting to the bottom 204 of the protuberance portion 201, the lower portion 215 having cross-sectional areas 217 along the longitudinal axis 205, wherein the cross-sectional area 208 at the bottom 204 of the protuberance portion 201 is greater than the cross-sectional area 218 of the lower portion 215 where the lower portion 215 connects to the bottom 204 of the protuberance portion 201; and a plurality of marks 209 disposed on the upper portion 211, protuberance portion 201, and lower portion 215, each mark 209 indicating a relative longitudinal location measured from the first end 212; wherein the upper portion 211 and lower portion 215 are configured to enable a break, when inserted in a length adjustable tubular retractor 100, at a selected predetermined position 220 on the length adjustable tubular retractor 100 by an action of breaking, wherein the action of breaking is accomplished by hands of the operator gripping the length adjustable tubular retractor 100 and tube breaker and applying force or moment to induce bending moment greater than the bending moment the selected predetermined position 220 on the length adjustable tubular retractor 100 can withstand.

Figure 2:
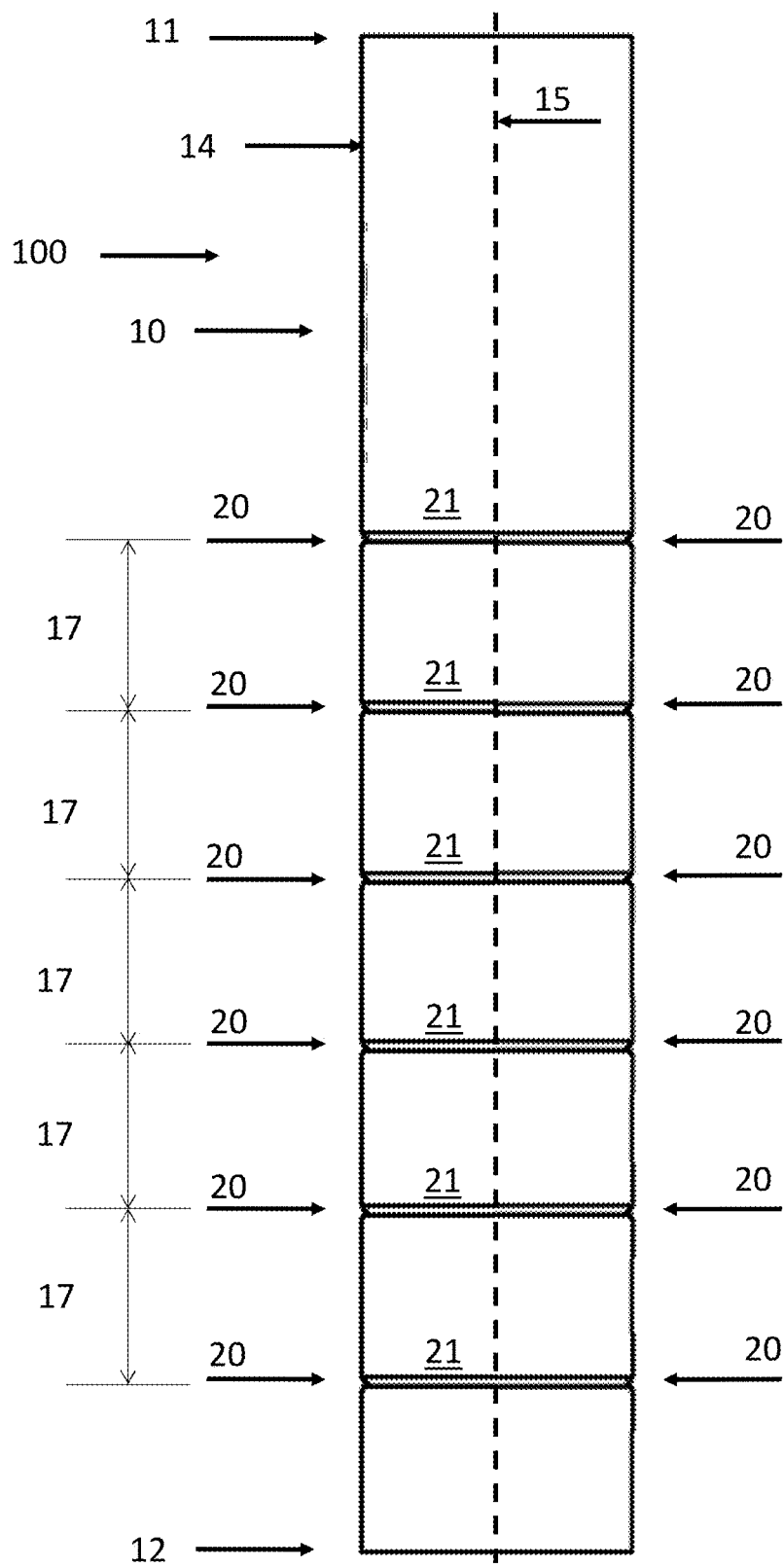
FIG. 2 is an elevation view of the length adjustable tubular retractor shown in FIG. 1.

Referring now to FIG. 2, in one embodiment, a disposable length adjustable tubular retractor 100 includes a cylindrical body 10 having a proximal end 11, distal end 12, internal surface 13, and exterior surface 14, the internal surface 13 facing toward a central axis 15 of the cylindrical body 10, the exterior surface 14 facing away from the central axis 15 of the cylindrical body 10, wherein the cylindrical body 10 has cross sections 16 along the central axis 15; and at least one exterior groove 20 circumferentially disposed along the exterior surface 14 of the cylindrical body 10 between the proximal end 11 and the distal end 12, the at least one exterior groove 20 disposed at a predetermined position 21 along the central axis 15 from the proximal end 11 to the distal end 12, wherein the at least one exterior groove 20 is configured such that the cylindrical body 10 is breakable at each of the predetermined positions 21 to form a size-selected disposable length adjustable tubular retractor 101.

Figure 3:
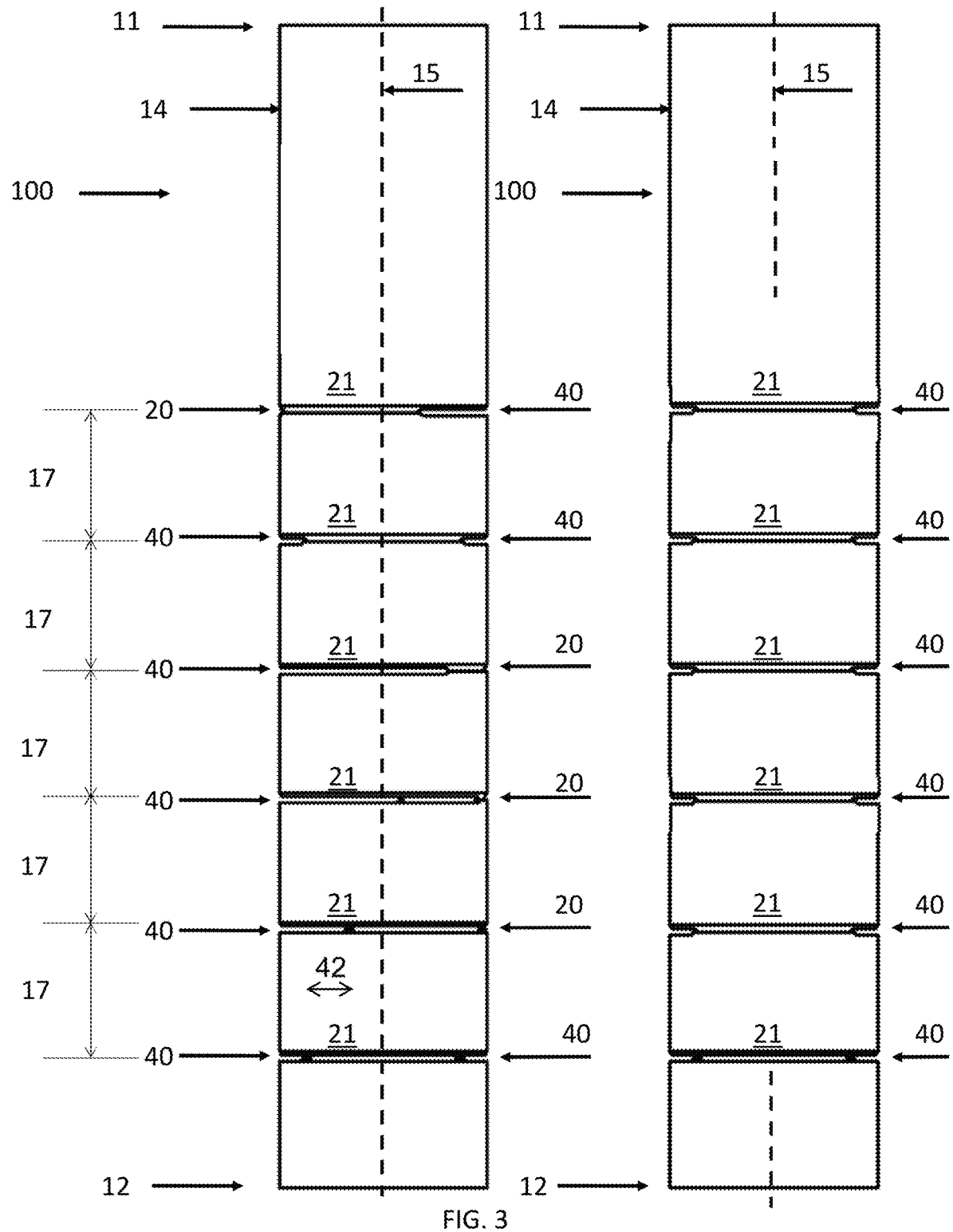
FIG. 3 is showing elevation views of another exemplary length adjustable tubular retractor.

Referring now to FIG. 3, in another embodiment, a disposable length adjustable tubular retractor 100 includes a cylindrical body 10 having a proximal end 11, distal end 12, internal surface 13, and exterior surface 14, the internal surface 13 facing toward a central axis 15 of the cylindrical body 10, the exterior surface 14 facing away from the central axis 15 of the cylindrical body 10, wherein the cylindrical body 10 has cross sections 16 along the central axis 15; at least one exterior groove 20 circumferentially disposed along the exterior surface 14 of the cylindrical body 10 between the proximal end 11 and the distal end 12, the at least one exterior groove 20 disposed at a predetermined position 21 along the central axis 15 from the proximal end 11 to the distal end 12, wherein the at least one exterior groove 20 is configured such that the cylindrical body 10 is breakable at each of the predetermined positions 21 to form a size-selected disposable length adjustable tubular retractor 101; and at least one of through slot 40 circumferentially disposed along the cylindrical body 10 between the proximal end 11 and the distal end 12, the at least one through slot 40 disposed at a predetermined position 21 along the central axis 15, wherein the at least one through slot 40 is configured such that the cylindrical body 10 is disconnected along and at each of the at least one through slot 40 and breakable at each of the predetermined positions 21 to form a size-selected disposable length adjustable tubular retractor 101.

Figure 5:
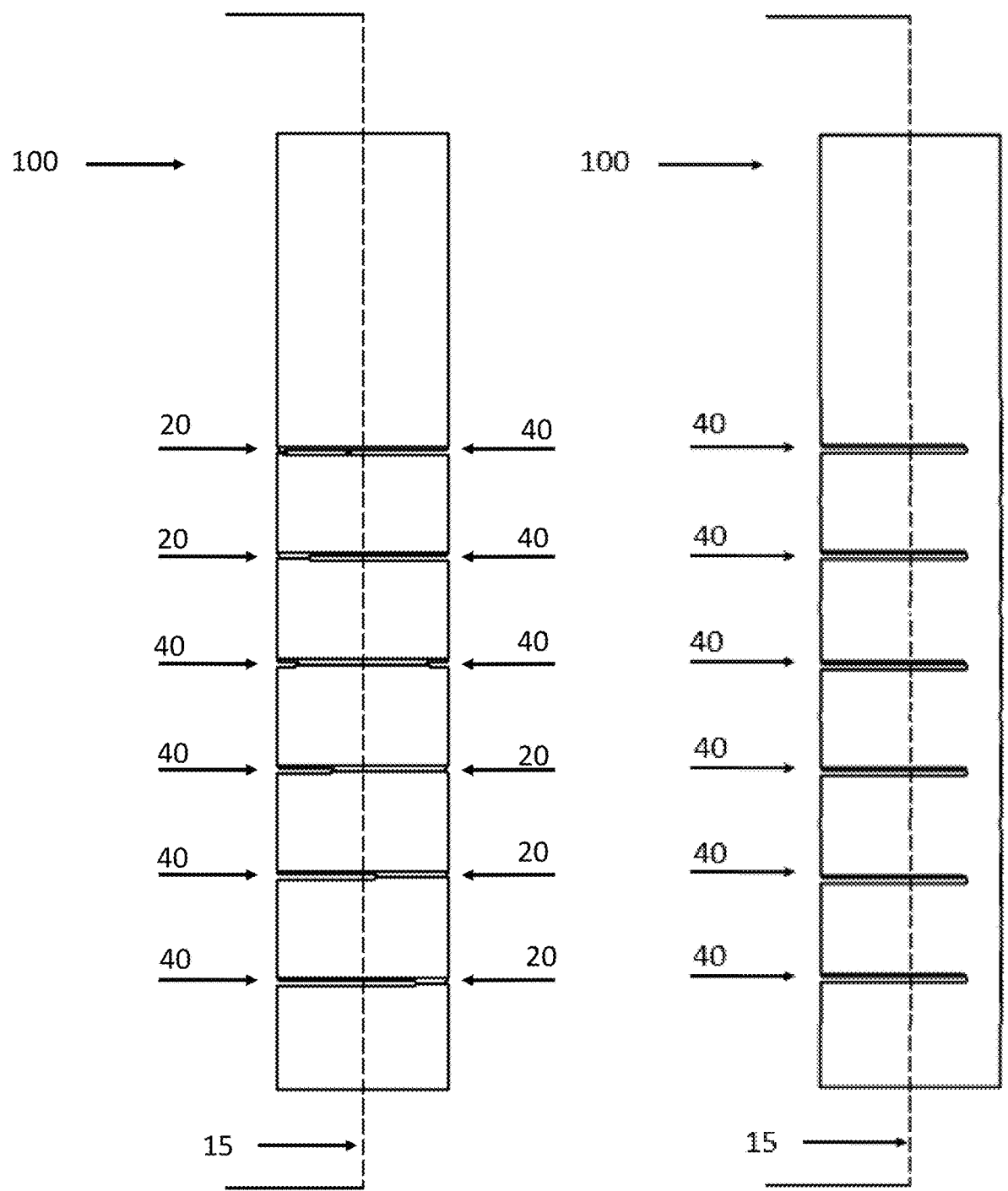
FIG. 5 is showing elevation views of other exemplary embodiments of a length adjustable tubular retractor.
Figure 14:
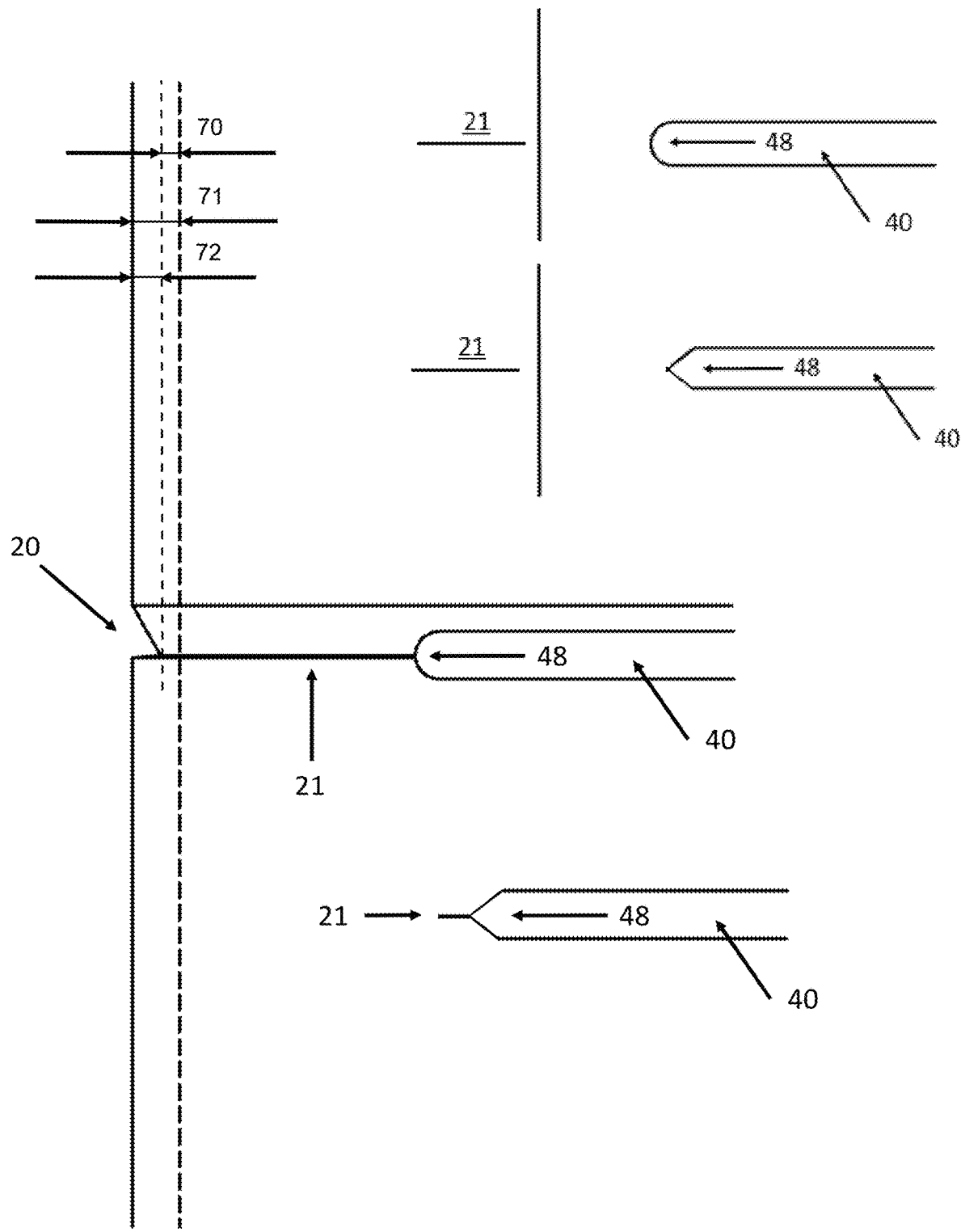
FIG. 14 is showing views illustrating a groove and through slot of an exemplary length adjustable tubular retractor at a predetermined position.

Referring now to FIGS. 5 and 14, in one embodiment, a disposable length adjustable tubular retractor 100 includes a cylindrical body 10 having a proximal end 11, distal end 12, internal surface 13, and exterior surface 14, the internal surface 13 facing toward a central axis 15 of the cylindrical body 10, the exterior surface 14 facing away from the central axis 15 of the cylindrical body 10, wherein the cylindrical body 10 has cross sections 16 along the central axis 15; and at least one of through slot 40 circumferentially disposed along the cylindrical body 10 between the proximal end 11 and the distal end 12, the at least one through slot 40 disposed at a predetermined position 21 along the central axis 15, wherein the at least one through slot 40 is configured such that the cylindrical body 10 is disconnected along and at each of the at least one through slot 40 and breakable at each of the predetermined positions 21 to form a size-selected disposable length adjustable tubular retractor 101.

Figure 4:
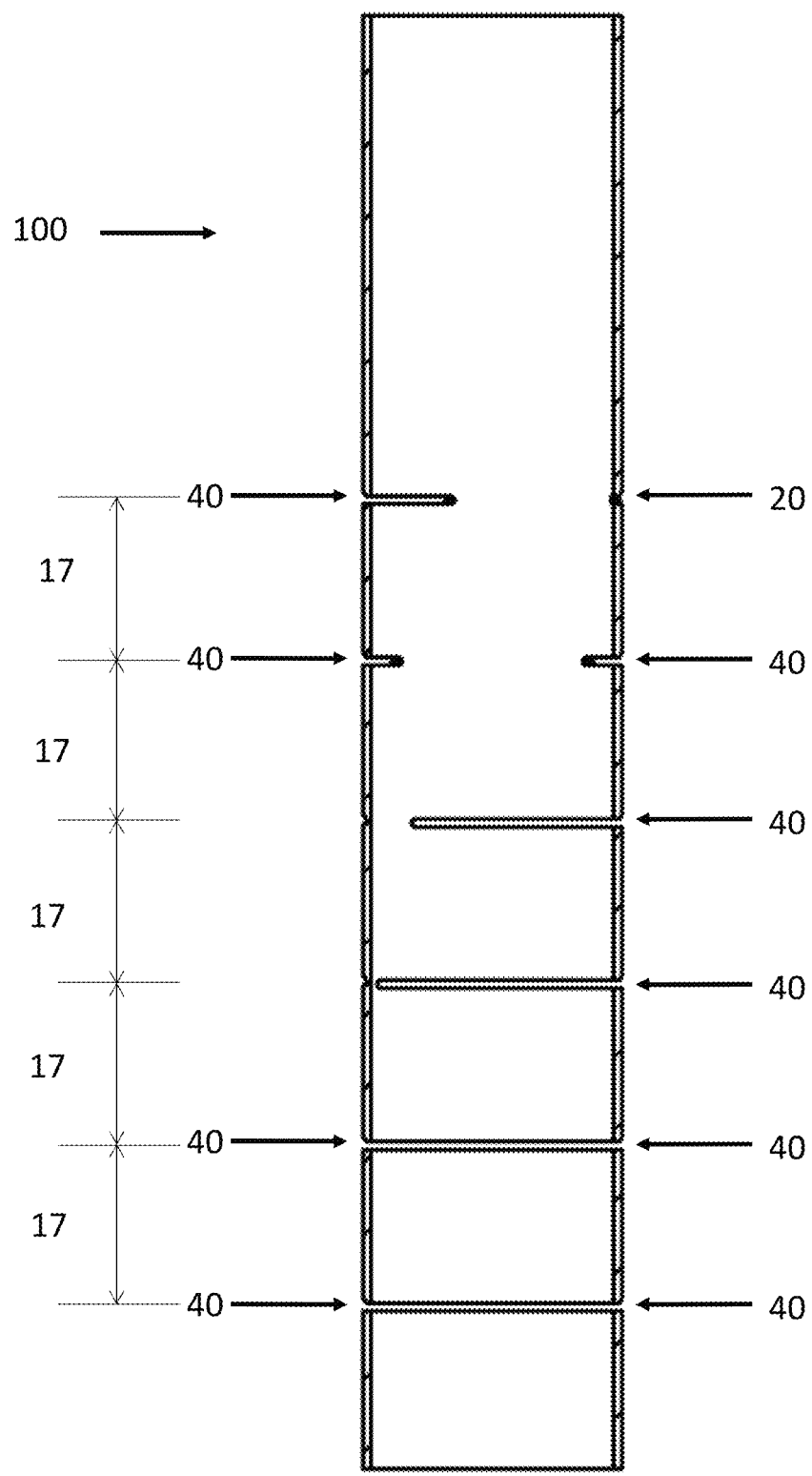
FIG. 4 is a view showing a vertical cross-section of an exemplary length adjustable tubular retractor.

Referring now to FIGS. 2-4, in one embodiment, the disposable length adjustable tubular retractor 100 may further include each predetermined position 21 spaced at a distance 17. Each predetermined position may be spaced equidistance 17. Each predetermined position 21 may be spaced equidistance 17 of approximately 5-15 mm. In another embodiment, each predetermined position 21 may be spaced equidistance 17 of approximately 10 mm. In another embodiment, each predetermined position 21 may be spaced non-equidistance 17. In another embodiment, a disposable length adjustable tubular retractor 100 may further include predetermined positions 21 spaced equidistance 17 and predetermined positions 21 spaced non-equidistance 17.

Figure 10:
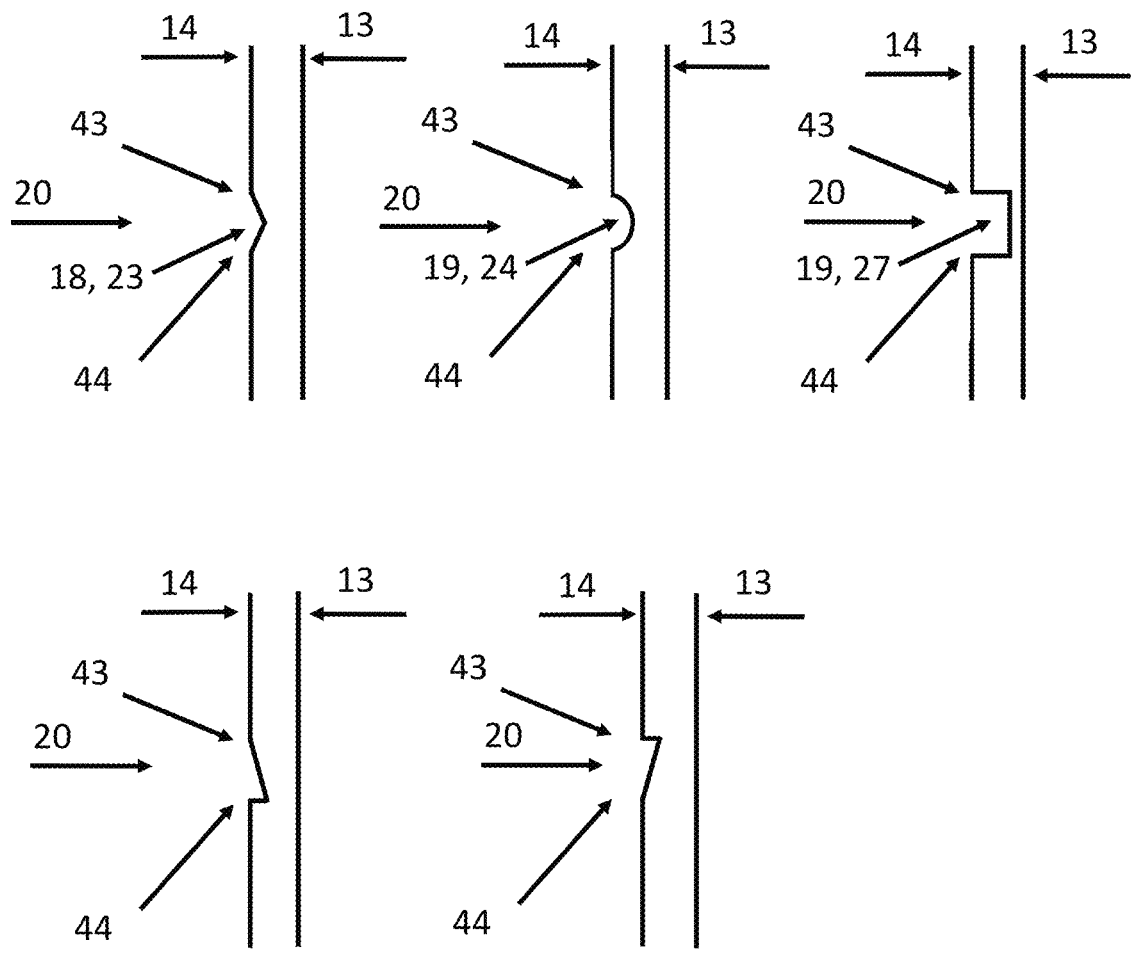
FIG. 10 is showing various exemplary embodiments of a groove of a length adjustable tubular retractor.
Figure 11A:
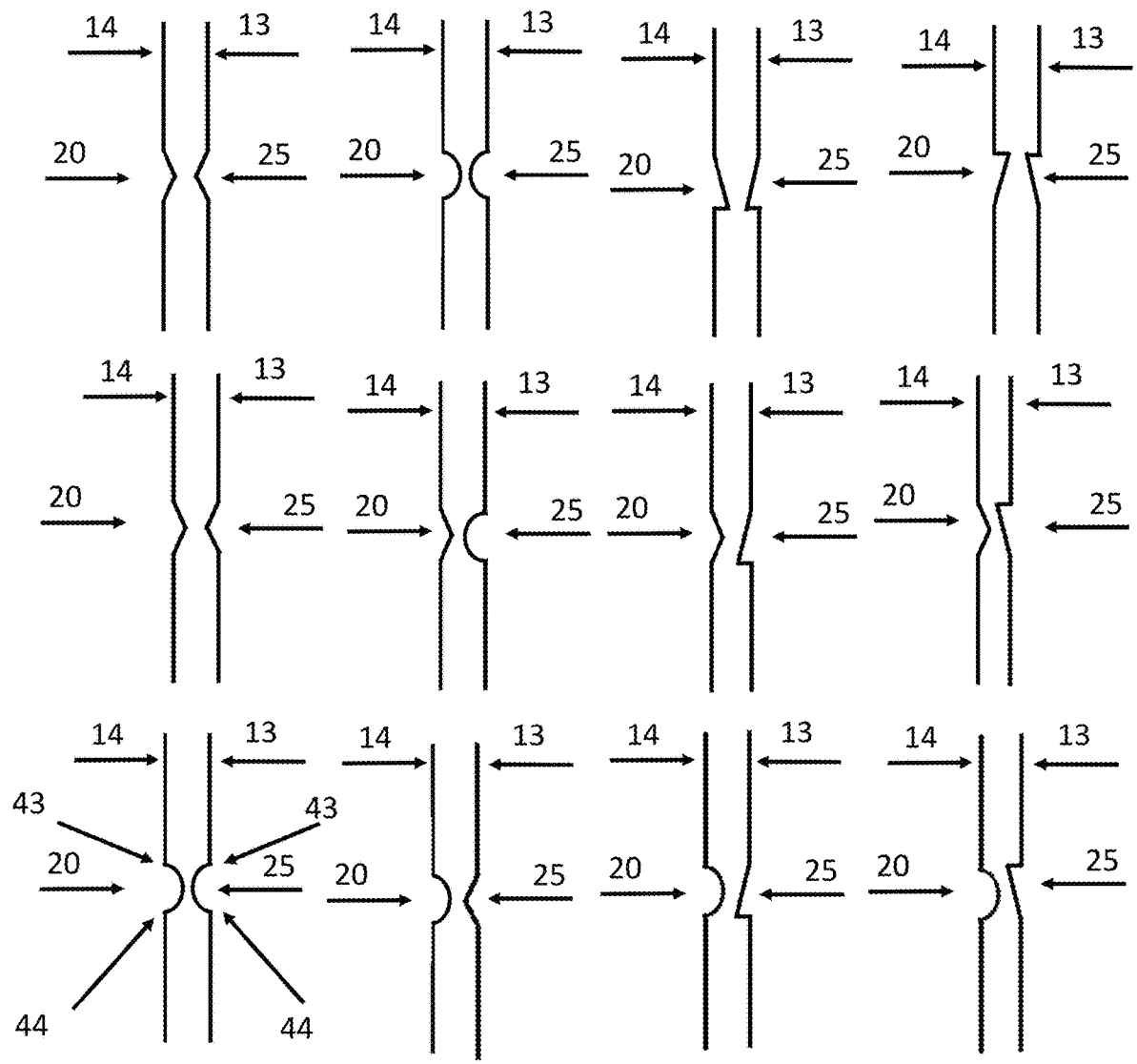
FIGS. 11A and 11B are showing various exemplary embodiments of a groove and interior groove of a length adjustable tubular retractor.
Figure 11B:
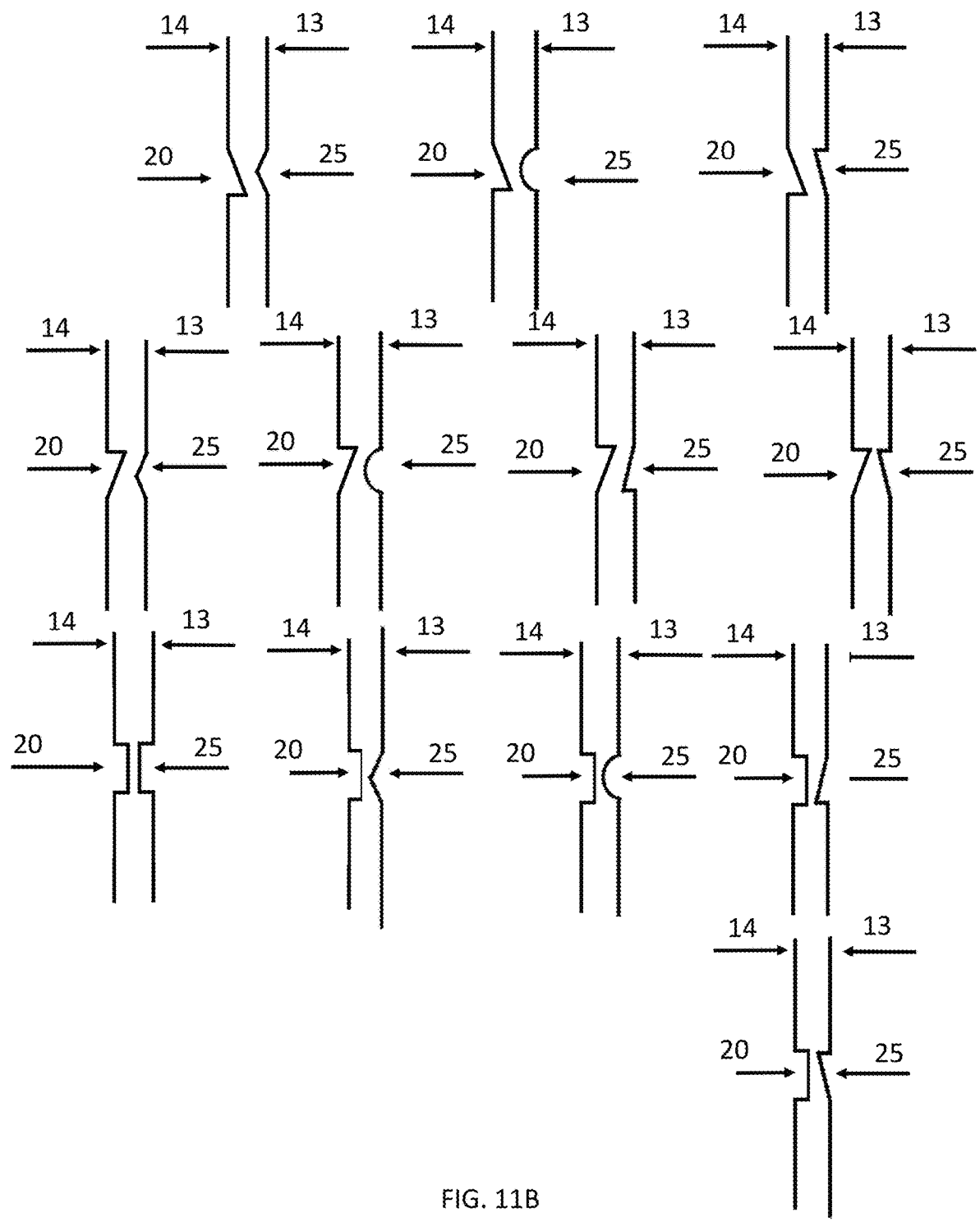
Figure 12:
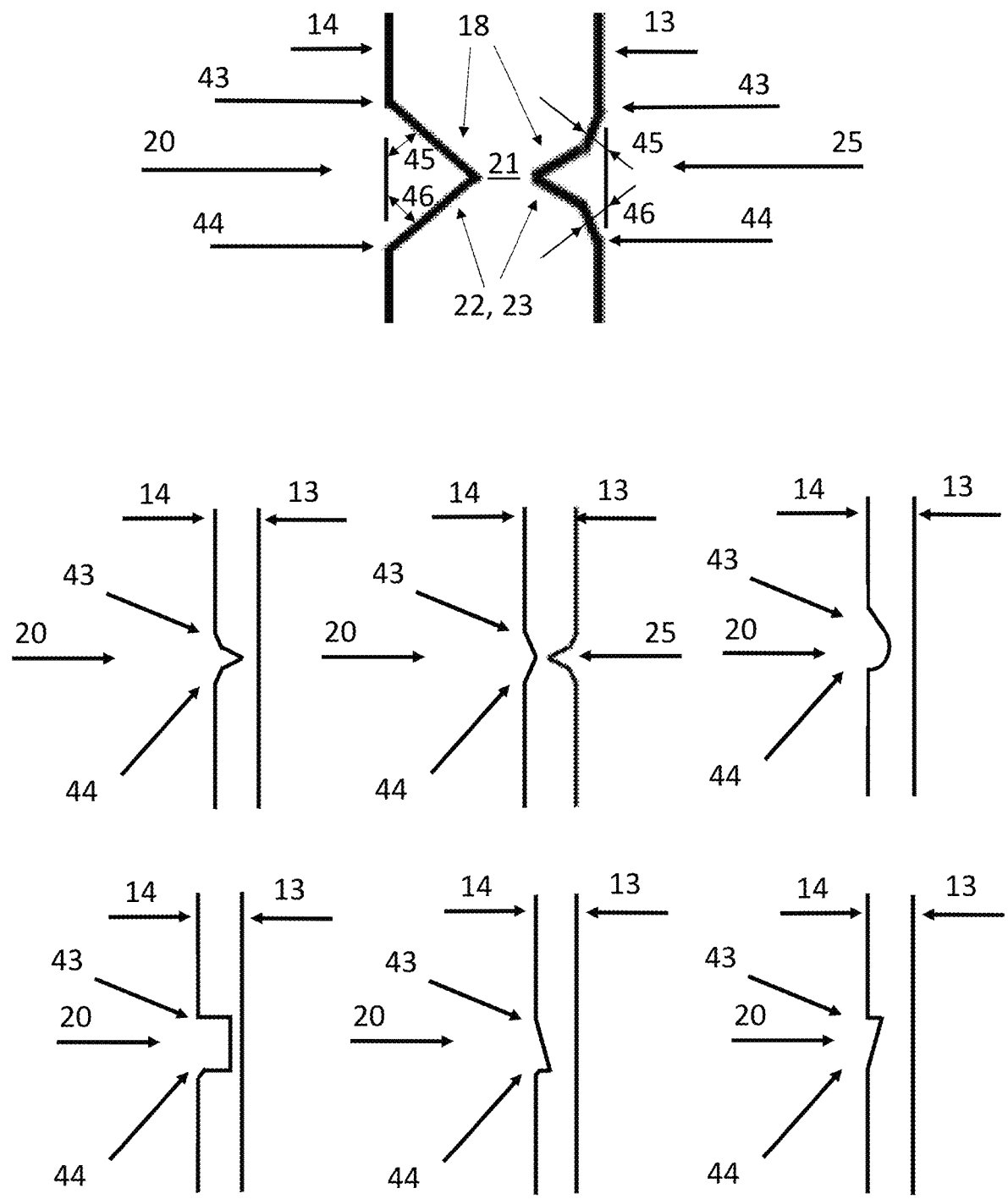
FIG. 12 is showing other exemplary embodiments of a groove and interior groove of a length adjustable tubular retractor.

Referring now to FIGS. 10-12, in one embodiment, a disposable length adjustable tubular retractor 100 may further include at least one exterior groove 20 comprising a V-shape 18, the V-shape 18 having an angle 22 at its apex 23 along the exterior surface 14. The angle 22 may be between about 15° and about 115°. In another embodiment, the angle 22 may be about 65°.

Referring now to FIGS. 10-12, in one embodiment, a disposable length adjustable tubular retractor 100 may further include at least one exterior groove 20 comprising a U-shape 19. The U-shape 19 may have a curvature 24 along the exterior surface 14. Referring now to FIGS. 10-12, in one embodiment, a disposable length adjustable tubular retractor 100 may further include at least one exterior groove 20 comprising a U-shape 19, the U-shape 19 having right angles 27 along the exterior surface 14.

Referring now to FIGS. 10-12, in one embodiment, a disposable length adjustable tubular retractor 100 may further include at least one exterior groove 20, the at least one exterior groove 20 further comprising a proximal edge 43 and distal edge 44.

Referring now to FIG. 12, in one embodiment, a disposable length adjustable tubular retractor 100 may further include at least one exterior groove 20, wherein the at least one exterior groove 20 may taper from the proximal edge 43 to the corresponding predetermined position 21 at a first taper angle 45 and taper from the distal edge 44 to the corresponding predetermined position 21 at a second taper angle 46. Each of the taper angles (45, 46) may be between about 0° and about 90°. Taper angles (45, 46) at a corresponding predetermined position may be identical. Taper angles (45, 46) at a corresponding predetermined position may be different than one another.

Referring now to FIGS. 10-12, in one embodiment, a disposable length adjustable tubular retractor 100 may further include at least one exterior groove 20, wherein the at least one exterior groove 20 may taper from the proximal edge 43 to the corresponding predetermined position 21 continuously at a first taper angle 45 and taper from the distal edge 44 to the corresponding predetermined position 21 continuously at a second taper angle 46 such that the exterior groove 20 includes a V-shape 18, the V-shape 18 having an angle 22 at its apex 23 along the exterior surface 14. Each of taper angles (45, 46) may be between about 0° and about 90°. Taper angles (45, 46) at a corresponding predetermined position may be identical. Taper angles (45, 46) at a corresponding predetermined position may be different than one another.

Referring now to FIGS. 10-12, in one embodiment, a disposable length adjustable tubular retractor 100 may further include at least one exterior groove 20, wherein a second taper angle 46 is about 90°, and a first taper angle 45 is about 30° such that an exterior surface 14 near a distal edge 44 is about normal to the central axis 15. In another embodiment, a disposable length adjustable tubular retractor 100 may further include at least one exterior groove 20, wherein a first taper angle 45 is about 90°, and a second taper angle 46 is about 30° such that an exterior surface 14 near a proximal edge 43 is about normal to the central axis 15.

Referring now to FIGS. 11A-12, in one embodiment, a disposable length adjustable tubular retractor 100 may further include at least one interior groove 25 disposed circumferentially along the internal surface 13 of the cylindrical body 10 between the proximal end 11 and the distal end 12, the at least one interior groove 25 disposed at a predetermined position 21 along the central axis 15 from the proximal end 11 to the distal end 12.

Referring now to FIGS. 11A-12, in one embodiment, a disposable length adjustable tubular retractor 100 may further include at least one interior groove 25 comprising a V-shape 18, the V-shape 18 having an angle 22 at its apex 23 along the internal surface 13. The angle may be between about 15° and about 115°. In one embodiment, the angle may be about 65°.

Referring now to FIGS. 11A-12, in one embodiment, a disposable length adjustable tubular retractor 100 may further include at least one interior groove 25 comprising a U-shape 19. The U-shape 19 may have a curvature 24 along the internal surface 13. Referring now to FIGS. 11A-12, in another embodiment, a disposable length adjustable tubular retractor 100 may further include at least one interior groove 25 comprising a U-shape 19, the U-shape 19 having right angles 27 along the internal surface 13.

Referring now to FIGS. 11A-12, in one embodiment, a disposable length adjustable tubular retractor 100 may further include at least one interior groove 25, the at least one interior groove 25 further comprising a proximal edge 43 and distal edge 44.

Referring now to FIGS. 11A-12, in one embodiment, a disposable length adjustable tubular retractor 100 may further include at least one interior groove 25, wherein the at least one interior groove 25 may taper from the proximal edge 43 to the corresponding predetermined position 21 at a first taper angle 45 and taper from the distal edge 44 to the corresponding predetermined position 21 at a second taper angle 46. Each of the taper angles (45, 46) may be between about 0° and about 90°. Taper angles (45, 46) at a corresponding predetermined position may be identical. Taper angles (45, 46) at a corresponding predetermined position may be different than one another.

Referring now to FIGS. 11A-12, in one embodiment, a disposable length adjustable tubular retractor 100 may further include at least one interior groove 25, wherein the at least one interior groove 25 may taper from the proximal edge 43 to the corresponding predetermined position 21 continuously at a first taper angle 45 and taper from the distal edge 44 to the corresponding predetermined position 21 continuously at a second taper angle 46 such that the interior groove 25 includes a V-shape 18, the V-shape 18 having an angle 22 at its apex 23 along the internal surface 13. Each of the taper angles (45, 46) may be between about 0° and about 90°. Taper angles (45, 46) at a corresponding predetermined position may be identical. Taper angles (45, 46) at a corresponding predetermined position may be different than one another.

Referring now to FIGS. 11A-12, in one embodiment, a disposable length adjustable tubular retractor 100 may further include at least one interior groove 25, wherein a second taper angle 46 is about 90°, and a first taper angle 45 is about 30° such that an internal surface 13 near a distal edge 44 is about normal to the central axis 15. In another embodiment, a disposable length adjustable tubular retractor 100 may further include at least one interior groove 25, wherein a first taper angle 45 is about 90°, and a second taper angle 46 is about 30° such that an internal surface 13 near a proximal edge 43 is about normal to the central axis 15.

Referring now to FIGS. 3-5, 10-12, and 14, in one embodiment, a disposable length adjustable tubular retractor 100 may further include at least one predetermined position 21 comprising an exterior groove 20 and a through slot 40.

Referring now to FIGS. 3-5 and 10-13, in one embodiment, a disposable length adjustable tubular retractor 100 may further include at least one predetermined position 21 comprising an exterior groove 20, an interior groove 25, and a through slot 40.

Figure 13:
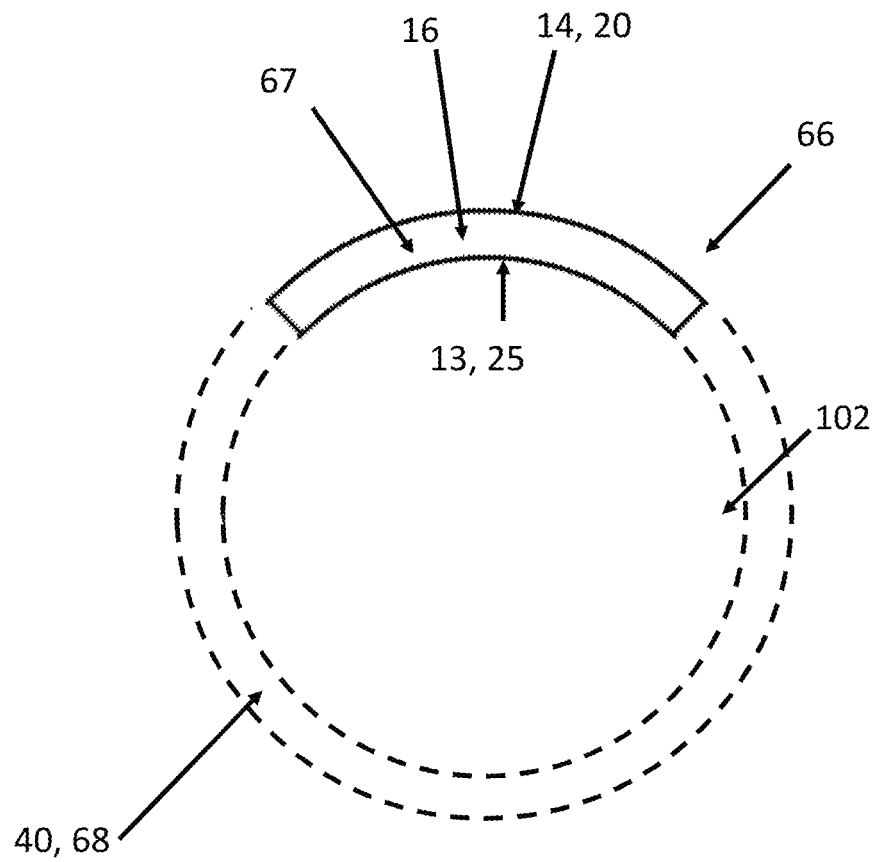
FIG. 13 is showing an exemplary cross section at a circumference of a length adjustable tubular retractor at a predetermined position.

Referring now to FIG. 13, in one embodiment, a disposable length adjustable tubular retractor 100 may have a ratio of a cross section 16 at a circumference 66 at each predetermined position 21, a ratio of a cross section 16 defined by a residual area 67, an area of a cross section 16 at a predetermined position 21, divided by a sum of the residual area 67 and a lost area 68 lost by at least one through slot 40 at a predetermined position 21.

A lost area 68 at a circumference 66 at a predetermined position 21 lost by at least one through slot 40 may range from about 10% to about 90%. Accordingly, a ratio of a cross section 16 may be between about 0.1 to 0.9. In one embodiment, a ratio of a cross section 16 is about 0.3.

Referring now to FIG. 14, in one embodiment, a disposable length adjustable tubular retractor 100 may have a residual thickness ratio at each predetermined position 21 where an exterior groove 20 or an interior groove 25 or both are disposed. A residual thickness ratio is defined by a residual thickness 70 of a cylindrical body 10 divided by a predetermined thickness 71 of the cylindrical body 10. A residual thickness 70 is measured by a predetermined thickness 71 minus the depth 72 of an exterior groove 20 or an interior groove 25, or depths 72 of both 20, 25 at a predetermined position 21. A depth 72 is defined as the distance from the outer surface penetrating the body 10 of the retractor 100 to a corresponding exterior groove 20 or interior groove 25.

A residual thickness ratio may be between about 0.1 and 1.0, where 1.0 means there is no exterior groove 20 or interior groove 25. In one embodiment, a predetermined thickness 71 is about 0.5 mm, and the depth 72 of an exterior groove 20 is about 0.3 mm; thus, the residual thickness 70 is 0.2 mm. Accordingly, the residual thickness ratio is about 0.4.

Referring now to FIG. 14, in one embodiment, a disposable length adjustable tubular retractor 100 may further include through slot ends 48 where a through slot 40 terminates. The through slot ends 48 may be configured to have a V-shape 18 or U-shape 19.

Figure 15:
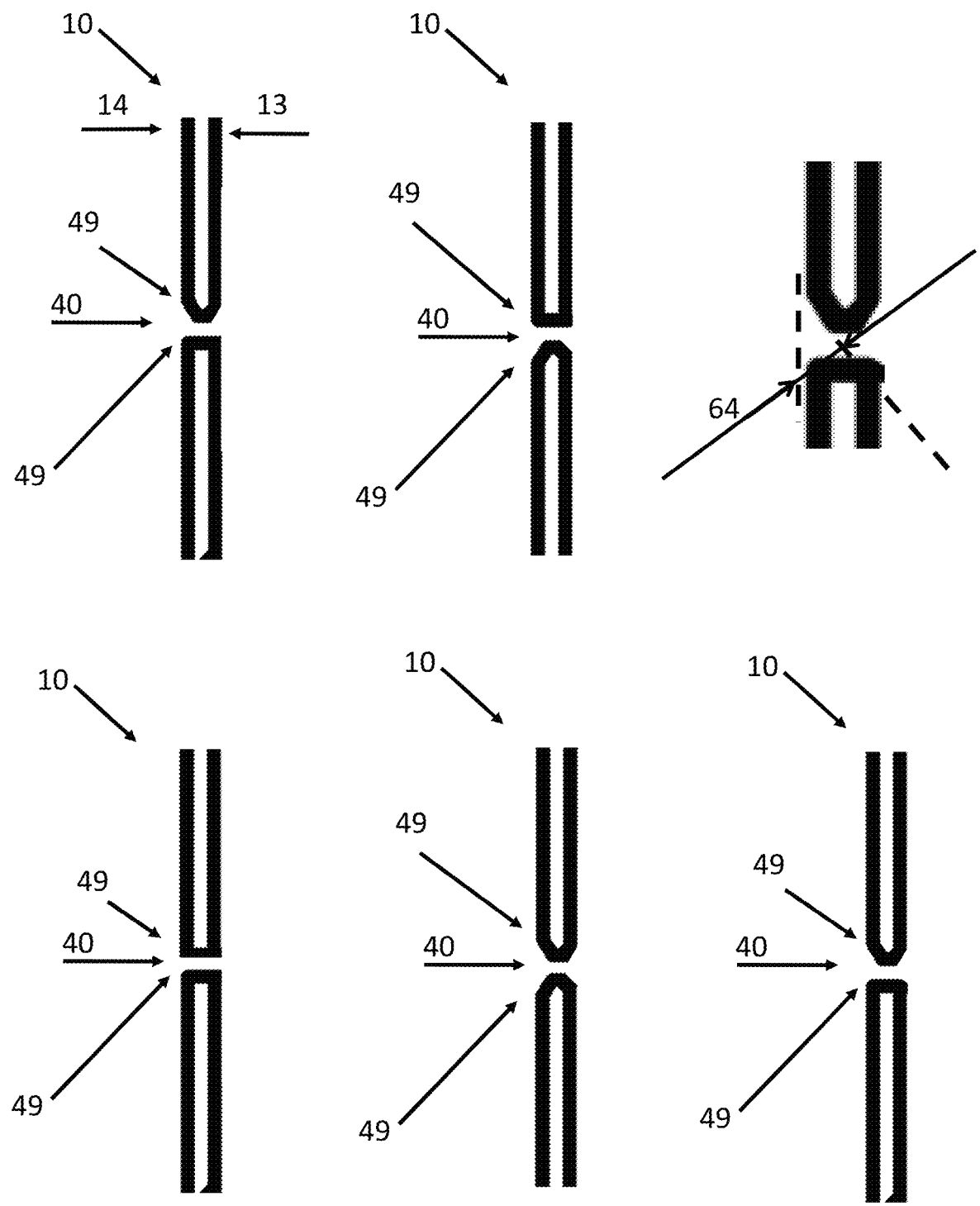
FIG. 15 is showing various exemplary embodiments of a through slot of a length adjustable tubular retractor at a predetermined position.

Referring now to FIG. 15, in one embodiment, a disposable length adjustable tubular retractor 100 may further include at least one through slot edge 49 where the cylindrical body 10 is disconnected along and at a through slot 40. A through slot edge 49 may be tapered from the exterior surface 14 to the corresponding through slot 40. In another embodiment, a through slot edge 49 may be tapered from the internal surface 13 to the corresponding through slot 40. A through slot edge 49 may be tapered at a through slot edge angle 64.

Referring now to FIG. 3, in one embodiment, a disposable length adjustable tubular retractor 100 may further include a plurality of through slots 40 disposed at a predetermined position 21 identically along the central axis 15 such that each of the plurality of through slots 40 at a predetermined position 21 overlaps along the central axis 15 with a through slot 40 at a different predetermined position 21.

Referring now to FIGS. 3-5, in one embodiment, a disposable length adjustable tubular retractor 100 may further include a plurality of through slots 40 disposed at a predetermined position 21 differently along the central axis 15.

Referring now to FIG. 3-5, in one embodiment, a disposable length adjustable tubular retractor 100 may further include a plurality of through slots 40 disposed at a predetermined position 21 differently such that each of the plurality of through slots 40 is disposed at a predetermined position 21 in a staggered arrangement along the central axis 15.

Referring now to FIGS. 3-5, in one embodiment, a disposable length adjustable tubular retractor 100 may further include a plurality of through slots 40 disposed at a predetermined position 21 differently such that each of the plurality of through slots 25 is disposed at a predetermined position in a spiral arrangement along the central axis 15.

Referring now to FIGS. 3-5, in one embodiment, a disposable length adjustable tubular retractor 100 may further include at least one through slot 40 disposed along the cylindrical body 10 from the distal end 12 toward the proximal end 11 at each predetermined position 21 such that a following through slot 40 is arranged to rotate an angle 42 about the central axis 15.

In one embodiment, a disposable length adjustable tubular retractor 100 may further include an angle 42 of about 30°.

Referring now to FIGS. 3-5, in one embodiment, a disposable length adjustable tubular retractor 100 may further include six through slots 40.

In one embodiment, a disposable length adjustable tubular retractor 100 may further include at least one predetermined position 21 comprising a plurality of through slots 40.

Figure 6:
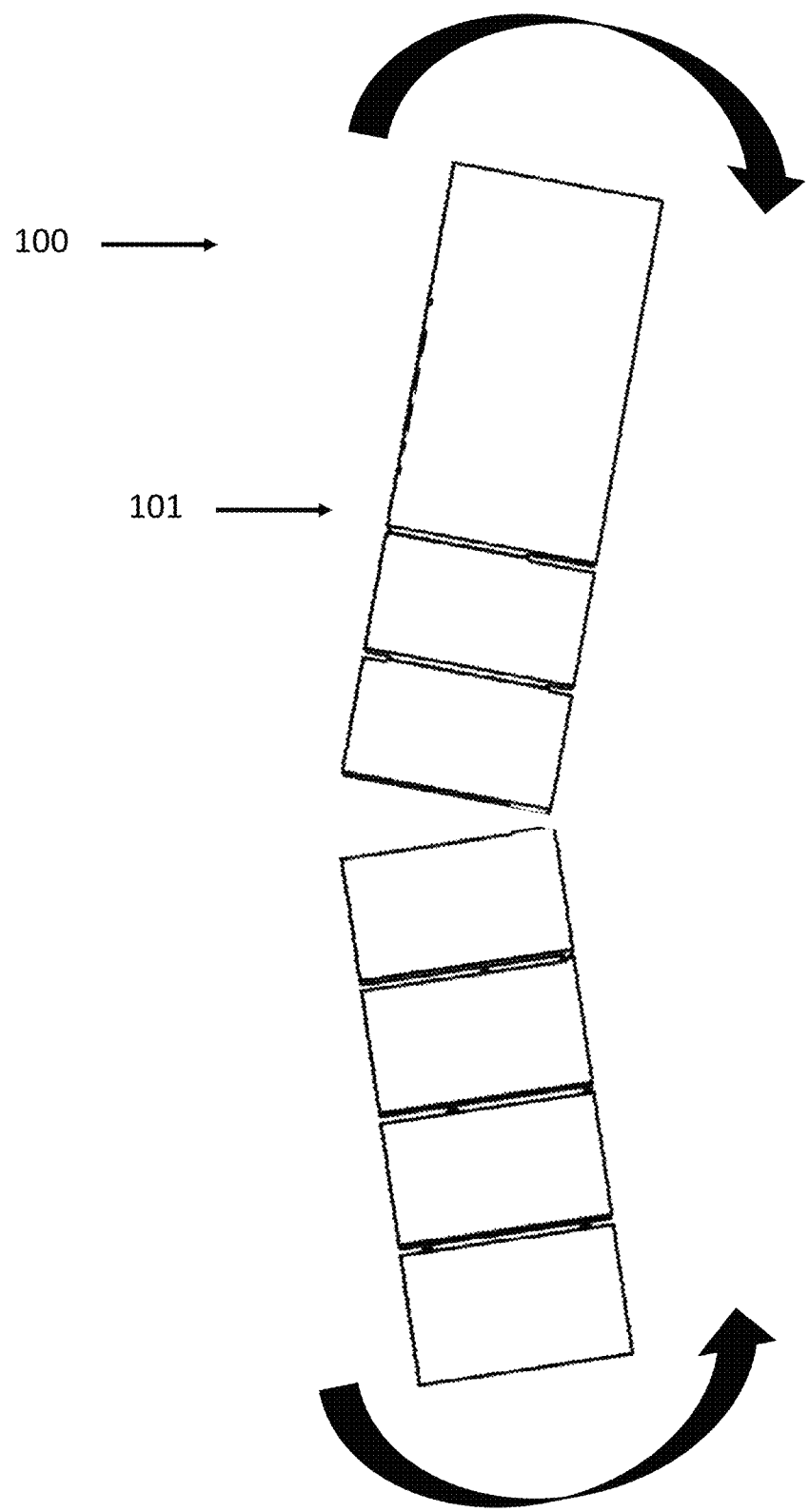
FIG. 6 is illustrating a break of an exemplary length adjustable tubular retractor at a predetermined position.

Referring now to FIG. 6, in one embodiment, a disposable length adjustable tubular retractor 100 is breakable at each predetermined position 21. The disposable length adjustable tubular retractor 100 may be manually breakable at each predetermined position 21. The disposable length adjustable tubular retractor 100 may be breakable at each predetermined position 21 by a breaker, a device configured to break a disposable length adjustable tubular retractor 100 at each predetermined position 21.

In one embodiment, a disposable length adjustable tubular retractor 100 may include a cylindrical body 10 comprised of titanium, stainless steel, polymer, or a combination thereof.

Figure 7:
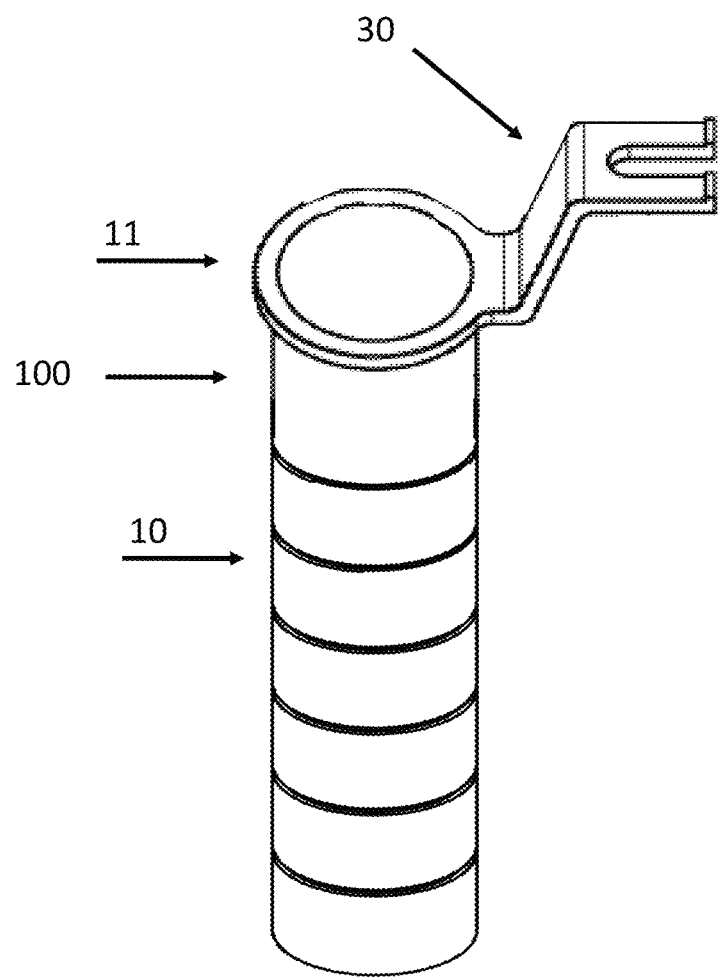
FIG. 7 is a view showing an exemplary length adjustable tubular retractor with a retractor arm.

Referring now to FIG. 7, in one embodiment, a disposable length adjustable tubular retractor 100 may further include a retractor arm 30 extending from the proximal end 11 of the cylindrical body 10.

Figure 8:
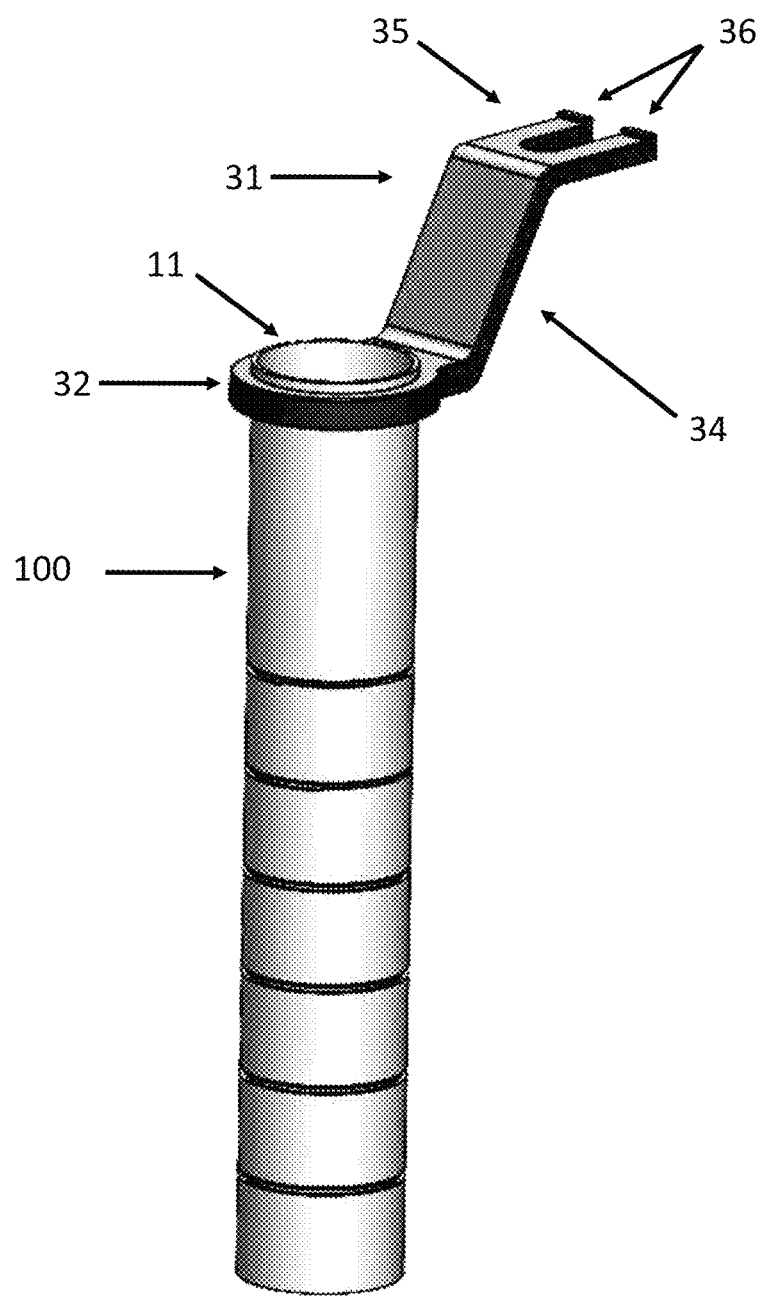
FIG. 8 is a view showing an exemplary length adjustable tubular retractor with a retractor handle.

Referring now to FIG. 8, in one embodiment, a disposable length adjustable tubular retractor 100 may further include a retractor handle 31, the retractor handle 31 comprising a ring 32 configured to be attached to the disposable length adjustable tubular retractor 100, the ring 32 formed directly onto the disposable length adjustable tubular retractor 100 such that the ring 32 is fixedly attached to the disposable length adjustable tubular retractor 100, and an arm 34 extending from the ring 32.

In one embodiment, a disposable length adjustable tubular retractor 100 may further include a retractor handle 31 comprised of titanium, stainless steel, polymer, or a combination thereof.

Referring now to FIG. 8, in one embodiment, a disposable length adjustable tubular retractor 100 may further include a retractor handle 31 disposed such that the proximal end 11 of the cylindrical body 10 protrudes from the retractor handle 31.

Referring now to FIG. 8, in one embodiment, a disposable length adjustable tubular retractor 100 may further include a frame 35 extending from a retractor handle 31, the frame 35 having two generally planar arms 36, the two generally planar arms 36 facing one another, the two generally planar arms 36 configured to be attached to a table arm, wherein the frame 35 is configured to receive a cylindrical fastening device such that the cylindrical fastening device clamps the frame 35 and fix the disposable length adjustable tubular retractor 100 thereby when the cylindrical fastening device engages in a fastening mode.

Figure 9:
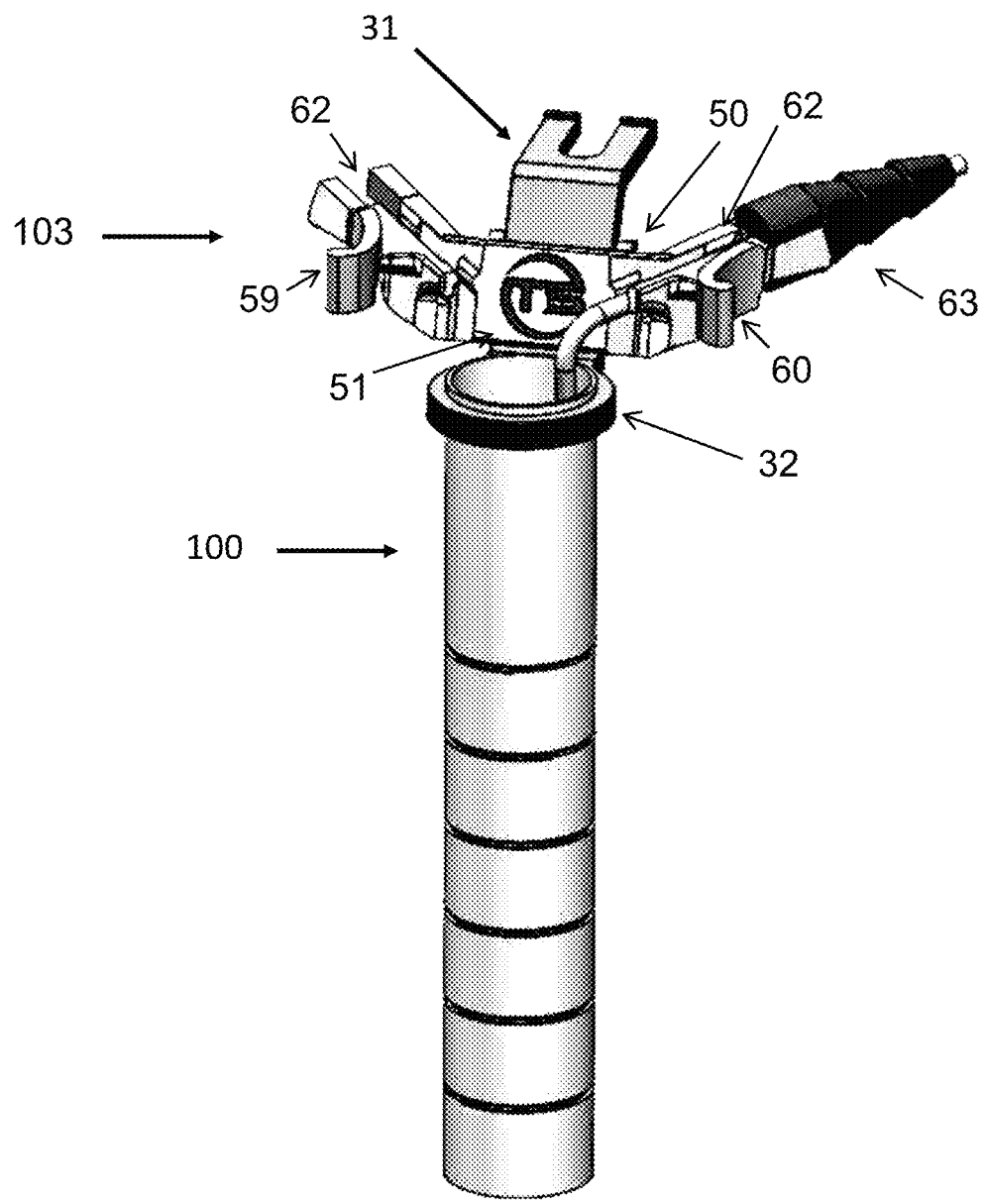
FIG. 9 is a view showing an exemplary surgical system.

Referring now to FIG. 9, in one embodiment, a surgical system 103 may include a disposable length adjustable tubular retractor 100; a retractor handle 31; and a mounting bracket 50, including: a plate 51; first and second arms 59, 60 adjacent to and extending from the of the plate 51; and at least one device emplacement 62 disposed adjacent to the plate 51 to receive and hold in-place a surgical tool 63 at a fixed position and orientation.

Referring now to FIG. 9, in another embodiment, a surgical system 103 may further include a frame 35 extending from the retractor handle 31, the frame 35 having two generally planar arms 36, the two generally planar arms 36 facing one another, the two generally planar arms 36 configured to be attached to a table arm, wherein the frame 35 is configured to receive a cylindrical fastening device such that the cylindrical fastening device clamps the frame 35 and fix the disposable length adjustable tubular retractor 100 thereby when the cylindrical fastening device engages in a fastening mode.

Also provided is a method for providing a size-selected length adjustable tubular retractor 101. The method includes providing a length adjustable tubular retractor 100 according to any one of a variety of embodiments as described above and herein, selecting one of the predetermined positions along the cylindrical body at which to break the retractor, and engaging a tool to enable a break at the selected predetermined position at the groove, through slot or combination thereof located at the selected predetermined position.

In some embodiments of the method, the tool is a pair of human hands, one hand disposed proximal to the selected predetermined position and the other hand disposed distal to the selected predetermined position, each hand gripping the retractor along the central axis, and the action of breaking is accomplished by rotation of the hands off of the central axis to break the cylindrical body.

Yet, in other embodiments, the tool can be an apparatus, a tube breaker 200. Referring to FIGS. 16-19, a tube breaker 200 is used to enable a break of a length adjustable tubular retractor 100 according to any one of a variety of embodiments as described above and herein at a selected predetermined position 220.

A tube breaker is designed and configured to be employed at the operator's convenience. The tube breaker is adapted to be inserted into a length adjustable tubular retractor at one end or at both ends of the tube breaker at the operator's convenience.

Figure 16:
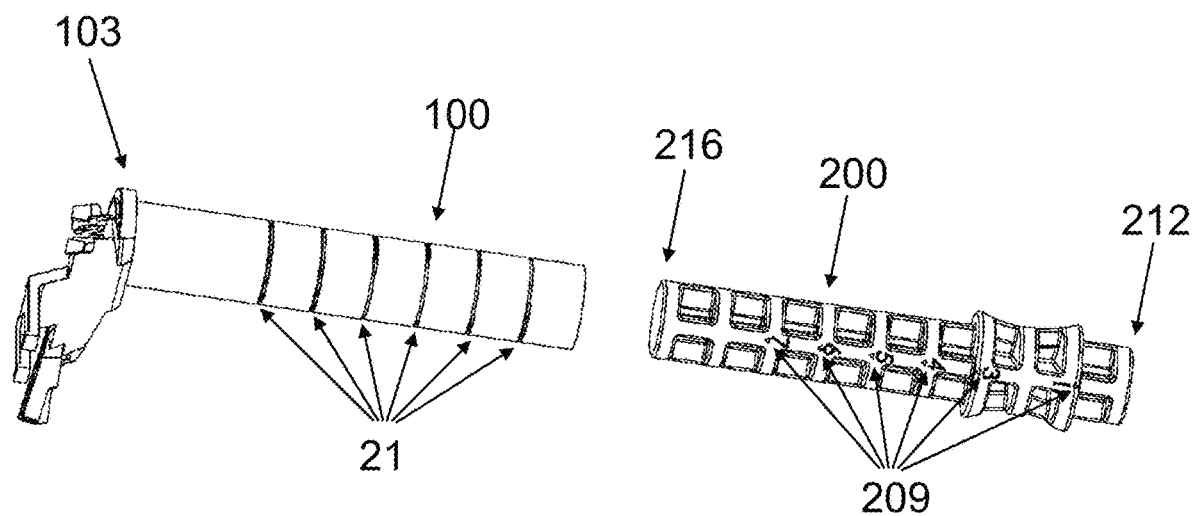
FIG. 16 is a view showing an exemplary surgical system including an exemplary length adjustable tubular retractor and an exemplary tube breaker.

Referring to FIG. 16, in one embodiment, a surgical system 103 including a length adjustable tubular retractor 100 and a tube breaker 200 including a first end 212 and a second end 216 is provided to enable a break at a predetermined position 21 selected by the operator on the length adjustable tubular retractor 100. It should be appreciated that other shapes may be employed. Marks 209 on the tube breaker 200 correspond to predetermined positions 21 on the length adjustable tubular retractor 100. For instance, in some embodiments, if each predetermined position 21 is spaced equidistance, the marks 209 are spaced correspondingly. In other embodiments, if each predetermined position 21 is spaced non-equidistance 17, the marks 209 are spaced correspondingly. Yet, in another embodiment, if a length adjustable tubular retractor 100 includes predetermined positions 21 spaced equidistance and predetermined positions 21 spaced non-equidistance, the marks 209 are spaced correspondingly.

In some embodiments, as shown in FIG. 16, marks 209 include pairs of marks 209, and a pair of marks 209 includes a scored triangle and a corresponding number. The number in each pair of marks 209 increases as each pair of marks 209 is disposed away from the first end 212 and toward the second end 216 along the tube breaker 200. Each mark 209 indicates a relative longitudinal location measured from the first end 212. It should be appreciated that other shapes and numbers of marks may be employed.

In some embodiments, as shown in FIG. 16, number 1 mark 209 communicates to the operator such that if the tube breaker 200 is inserted at the first end 212 into the length adjustable tubular retractor 100 until the length adjustable tubular retractor 100 reaches a scored triangle 218 that includes number 1, the tube breaker 200 is positioned to enable a break of one distance of the length adjustable tubular retractor 100 by employing and accomplishing an action of breaking. Number 7 mark 209 communicates to the operator such that if the tube breaker 200 is inserted at the second end 216 into the length adjustable tubular retractor 100 until the length adjustable tubular retractor 100 reaches a scored triangle 218 that includes number 7, the tube breaker 200 is positioned to enable a break of two distances of the length adjustable tubular retractor 100 by employing and accomplishing an action of breaking. Number 6 mark 209 communicates to the operator such that if the tube breaker 200 is inserted at the second end 216 into the length adjustable tubular retractor 100 until the length adjustable tubular retractor 100 reaches a scored triangle 218 that includes number 6, the tube breaker 200 is positioned to enable a break of three distances of the length adjustable tubular retractor 100 by employing and accomplishing an action of breaking. Number 5, 4, and 3 marks 209 communicate to the operator in the same way as number 7 and 6 marks 209 communicate to the operator as described above, and if the tube breaker 200 is inserted until corresponding marks 209, the tube breaker 200 is positioned to enable a break of four distances (number 5), or five distances (number 4), or six distances (number 5) of the length adjustable tubular retractor 100, respectively, by employing and accomplishing an action of breaking. It should be appreciated that other methods, sequences, and arrangements of marking may be employed.

Figure 17:
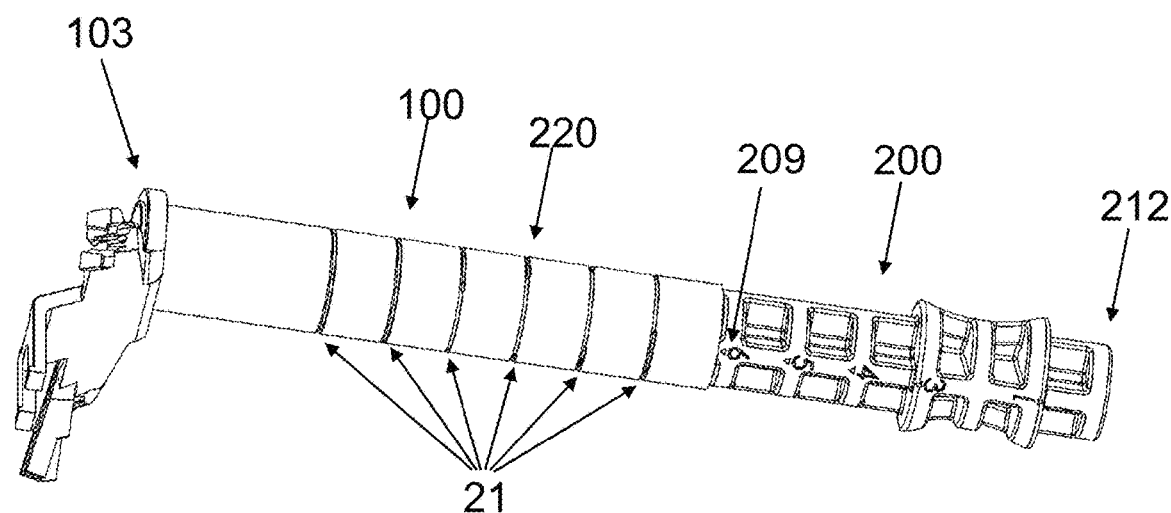
FIG. 17 is a view showing one end of the tube breaker shown in FIG. 16 is inserted into the length adjustable tubular retractor shown in FIG. 16 to enable a break at a predetermined position on the length adjustable tubular retractor.

Referring to FIG. 17, in one embodiment, a tube breaker 200 is inserted into a length adjustable tubular retractor 100 to enable a break at a predetermined position 21 where a groove and a through slot are disposed. More specifically, if the operator desires to break the length adjustable tubular retractor 100 at a predetermined position 21, i.e., a selected predetermined position 220, the second end (not shown) of the tube breaker 200 is inserted until the length adjustable tubular retractor 100 reaches at the corresponding marks 209, a scored triangle and number 6, which represent that the tube breaker 200 reached at the selected predetermined position 220 on the length adjustable tubular retractor 100 corresponding to a break of three distances of the length adjustable tubular retractor 100 if an action of breaking is employed and accomplished.

An action of breaking is accomplished when the operator grips the length adjustable tubular retractor and the tube breaker inserted into the length adjustable tubular retractor and applies force or moment to induce bending moment greater than the bending moment a predetermined position on the length adjustable tubular retractor can withstand. It should be appreciated that the bending moment a predetermined position on a length adjustable tubular retractor can withstand varies depending on the relative location of each predetermined position and the shapes, sizes, and property of material of the length adjustable tubular retractor.

Figure 18:
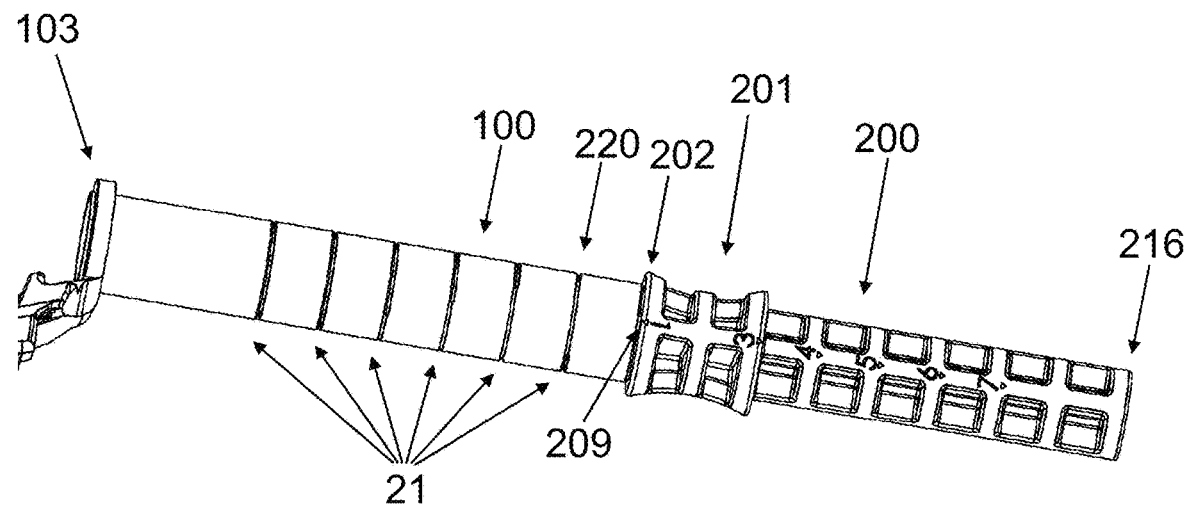
FIG. 18 is another view showing the other end of the tube breaker shown in FIG. 16 is inserted into the length adjustable tubular retractor shown in FIG. 16 to enable a break at a different predetermined position on the length adjustable tubular retractor.
Figure 19:
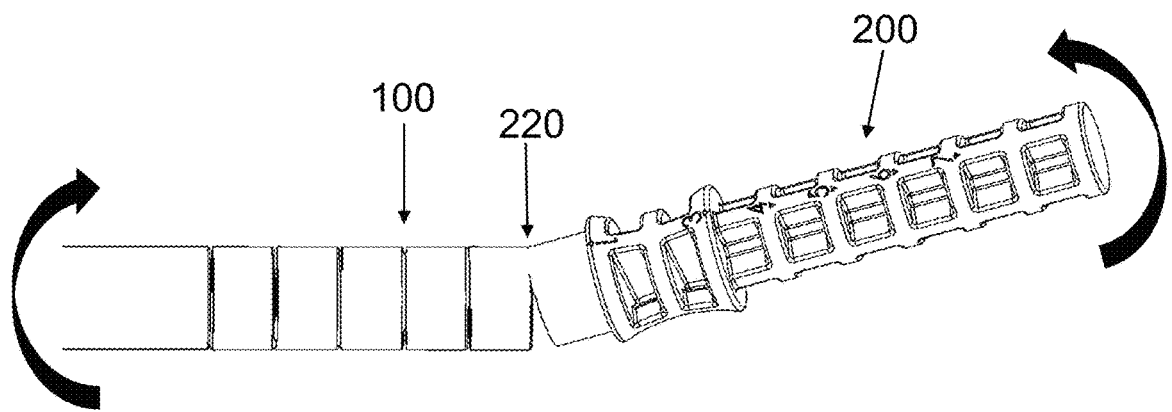
FIG. 19 is a view showing the tube breaker shown in FIG. 18 is breaking the length adjustable tubular retractor shown in FIG. 18 at the predetermined position when an action of breaking is employed.
Figure 20:
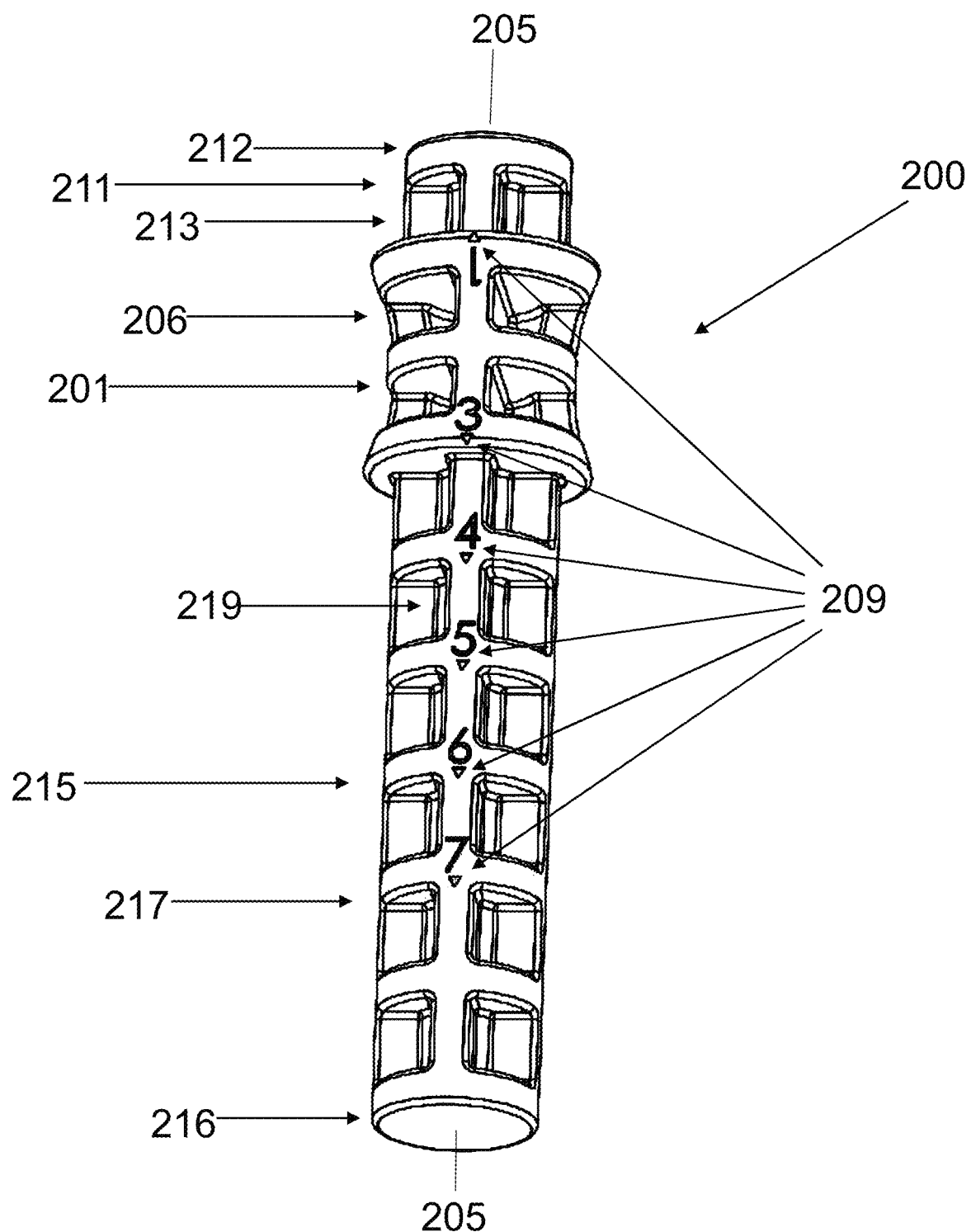
FIG. 20 is a lower bottom perspective view of the tube breaker shown in FIG. 16.
Figure 21:
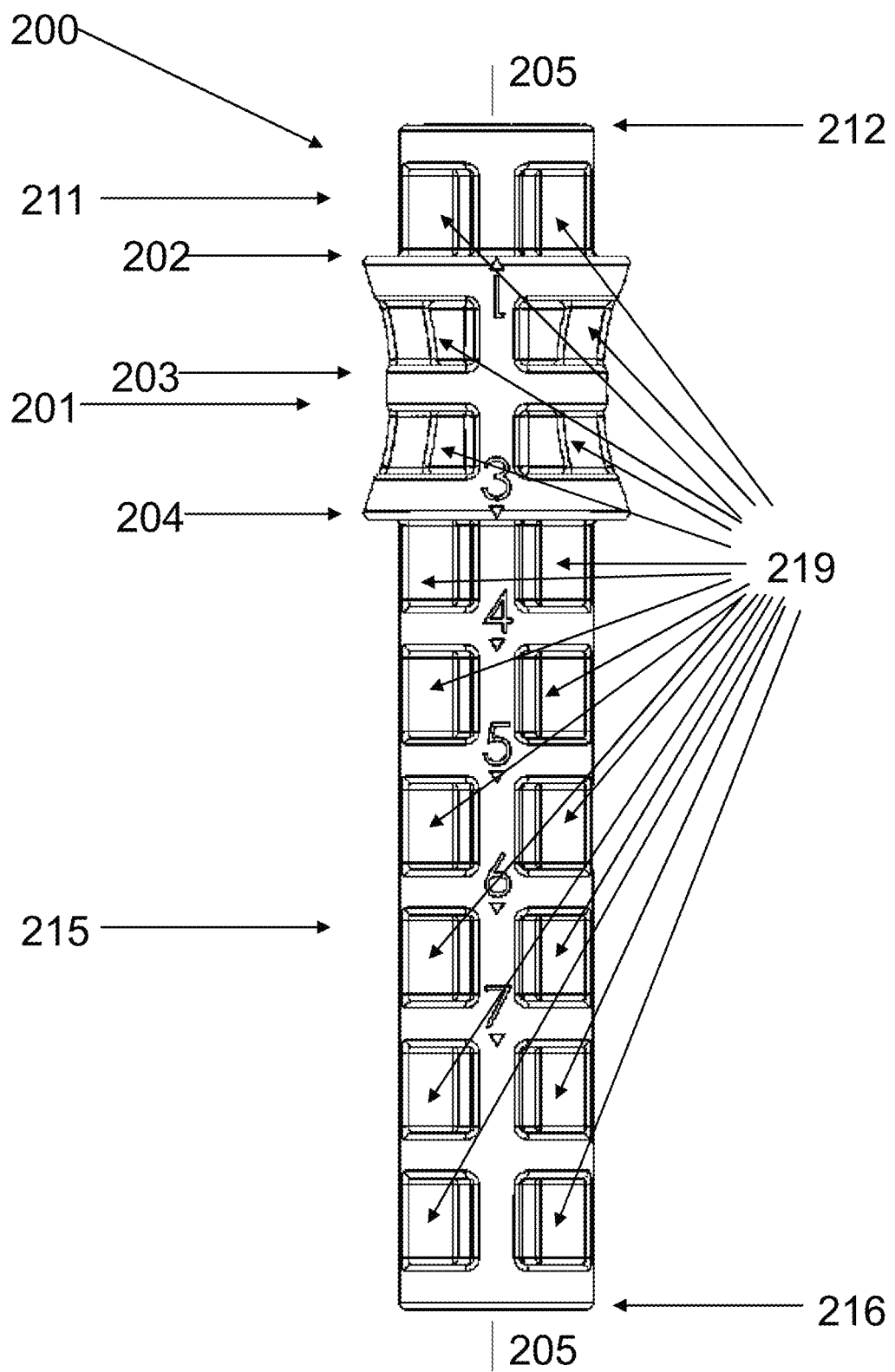
FIG. 21 is a front view of the tube breaker shown in FIG. 16.
Figure 22:
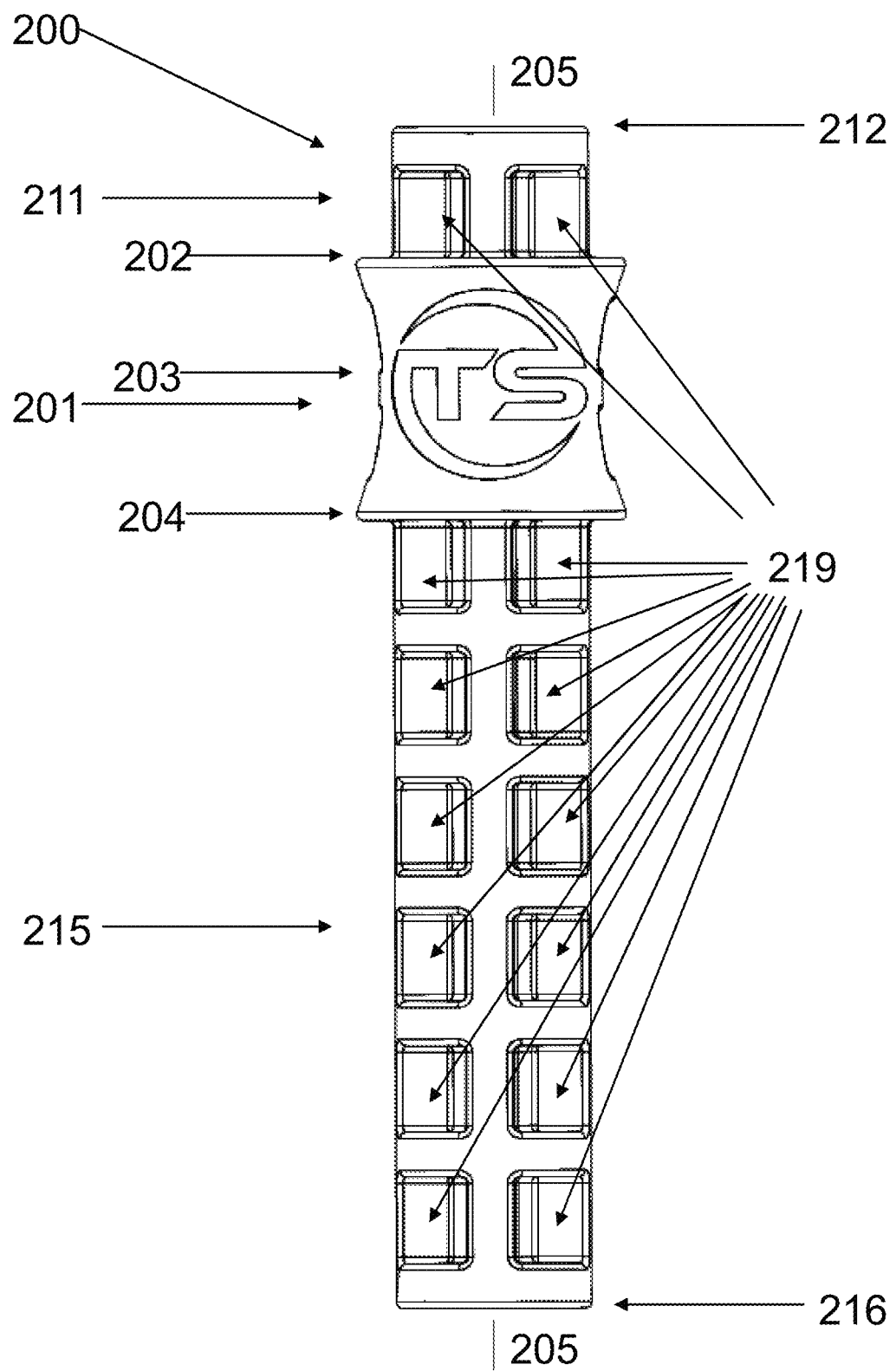
FIG. 22 is a rear view of the tube breaker shown in FIG. 16.
Figure 23:
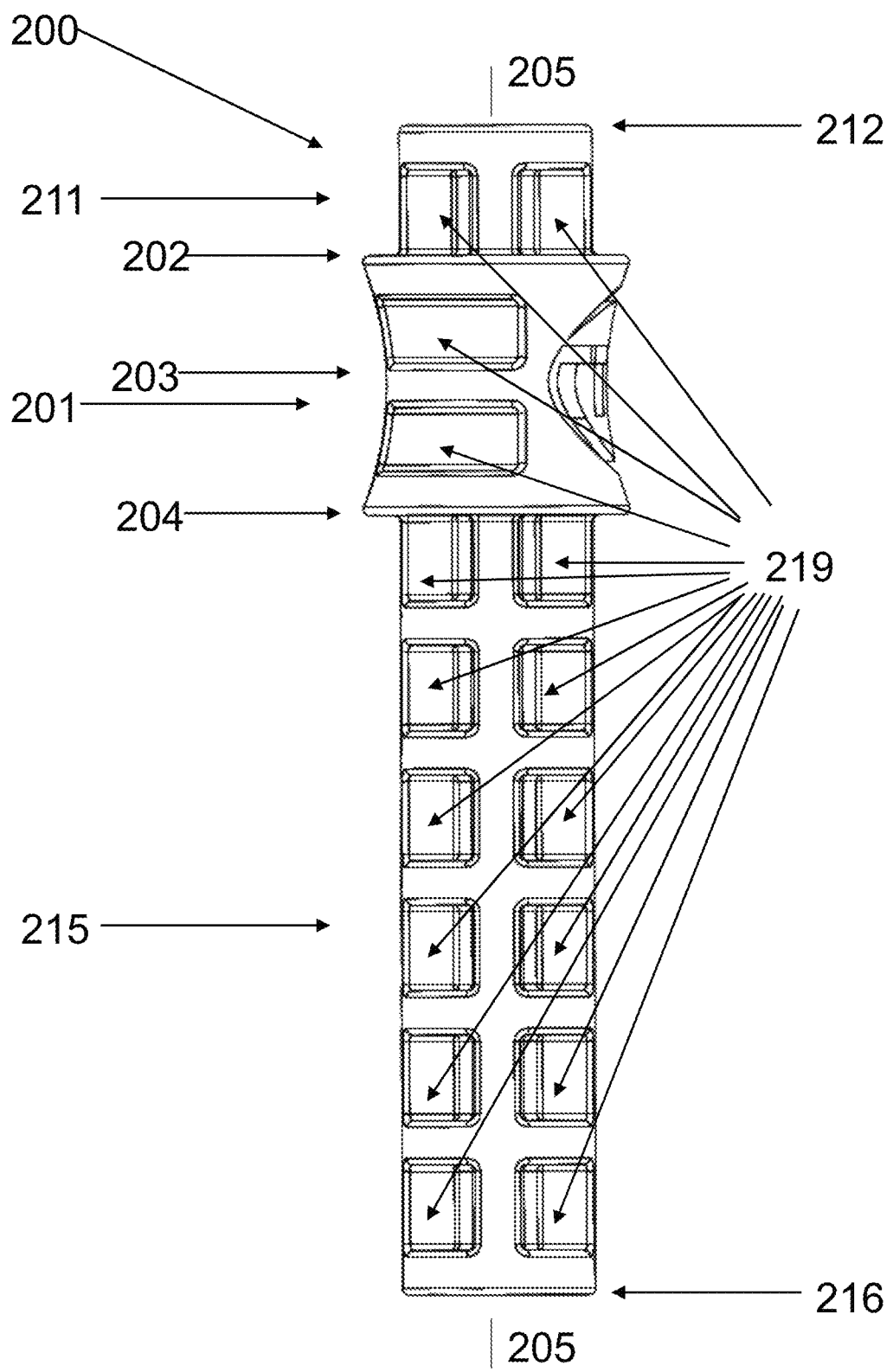
FIG. 23 is a right side elevation view of the tube breaker shown in FIG. 16.
Figure 24:
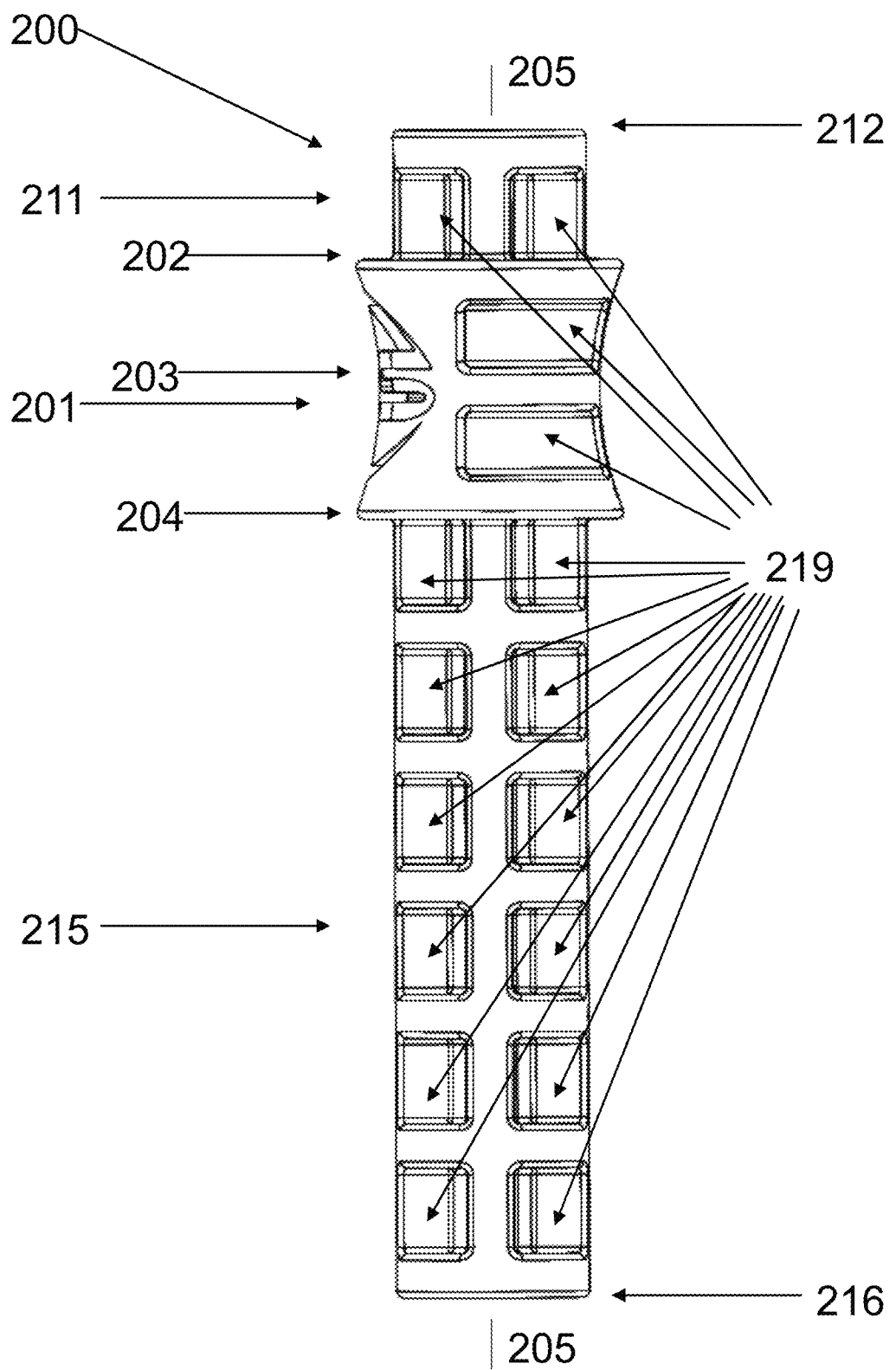
FIG. 24 is a left side elevation view of the tube breaker shown in FIG. 16.
Figure 25:
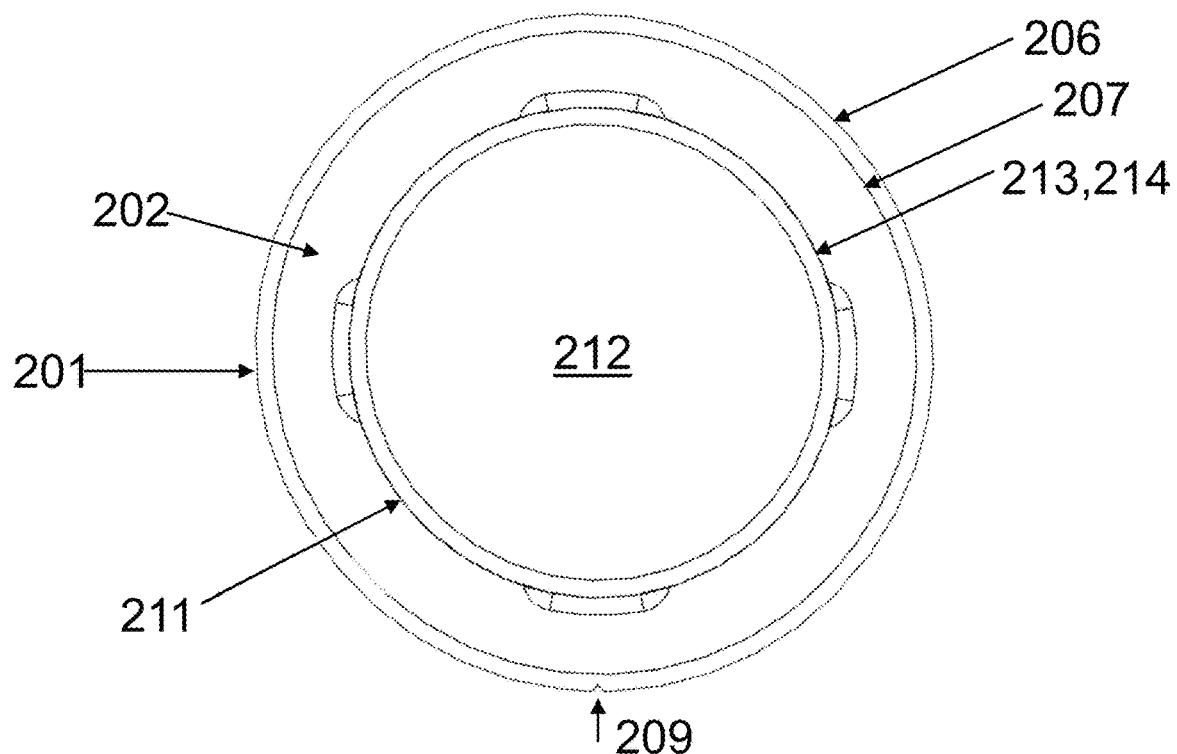
FIG. 25 is a top view of the tube breaker shown in FIG. 16.
Figure 26:
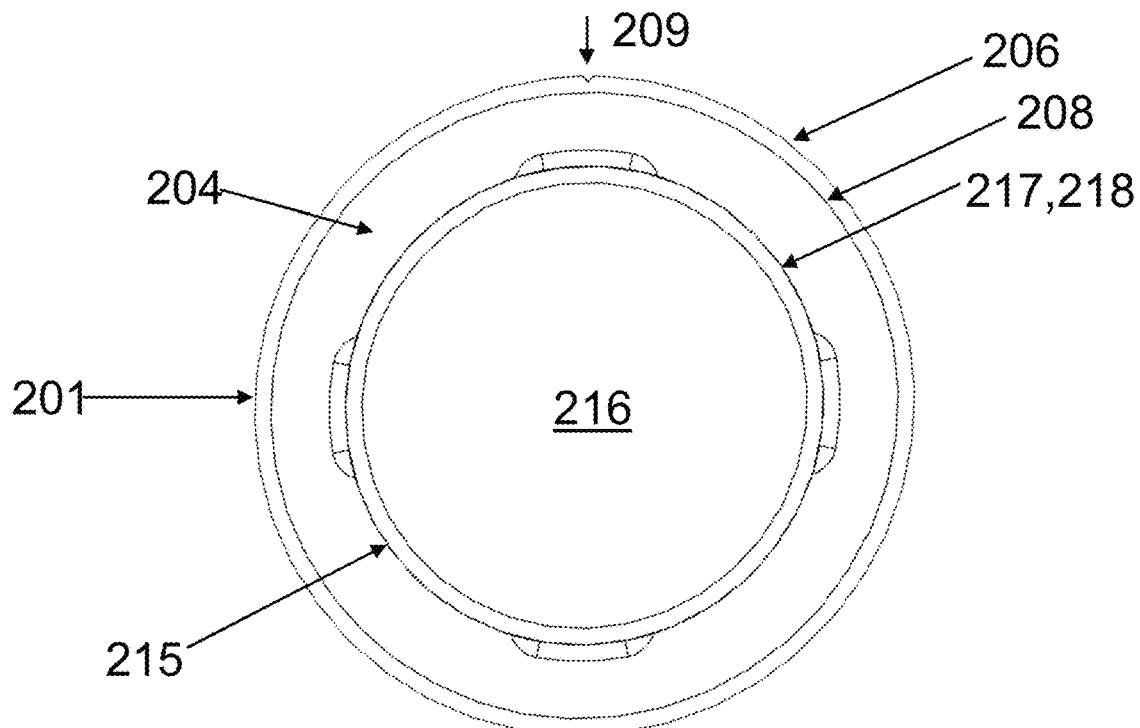
FIG. 26 is a bottom view of the tube breaker shown in FIG. 16.

Referring to FIGS. 18-19, in another embodiment, the first end 212 (not shown) of the tube breaker 200 is inserted until the length adjustable tubular retractor 100 reaches at the top 202 of the protuberance portion 201 where the marks 209 on the top 202 of the protuberance portion 201, the scored triangle and number 1, represent that the tube breaker 200 reached at a selected predetermined position 220 on the length adjustable tubular retractor 100 corresponding to a break of one distance of the length adjustable tubular retractor 100 if an action of breaking is employed and accomplished. Then, an action of breaking is employed (FIG. 19), and the break of one length of the length adjustable tubular retractor 200 at the selected predetermined position 220 is undergoing thereafter.

Referring to FIGS. 20-26, in one embodiment, a tube breaker 200 includes a protuberance portion 201, an upper portion 211, a lower portion body 215, and a plurality of marks 209. The protuberance portion 201 has a top 202, side 203, and bottom 204, the side 203 is disposed between the top 202 and the bottom 204, and the protuberance portion 201 extends from the top 202 toward the bottom 204 along a longitudinal axis 205. The protuberance portion 201 has cross-sectional areas 206 along the longitudinal axis 205. The upper portion 211 has a generally cylindrical shape and is adapted to be slidably inserted in a length adjustable tubular retractor (not shown). The upper portion 211 has a first end 212, extends from the first end 212 along the longitudinal axis 205 toward the protuberance portion 201, and connects to the top 202 of the protuberance portion 201.

The upper portion 211 has cross-sectional areas 213 along the longitudinal axis 205. The cross-sectional area 207 at the top 202 of the protuberance portion 201 is greater than the cross-sectional area 214 of the upper portion 211 where the upper portion 211 connects to the top 202 of the protuberance 201. The lower portion 215 has a generally cylindrical shape and is adapted to be slidably inserted in a length adjustable tubular retractor (not shown). The lower portion 215 has a second end 216, and the lower portion 215 extends from the second end 216 along the longitudinal axis 205 toward the protuberance portion 201 and connects to the bottom 204 of the protuberance portion 201. The lower portion 215 has cross-sectional areas 217 along the longitudinal axis 205, and the cross-sectional area 208 at the bottom 204 of the protuberance portion 201 is greater than the cross-sectional area 218 of the lower portion 215 where the lower portion 215 connects to the bottom 204 of the protuberance portion 201. The plurality of marks 209 is disposed on the upper portion 211, protuberance portion 201, and lower portion 215, and each mark 209 indicates a relative longitudinal location measured from the first end 212. In some embodiments, each mark 209 may be spaced equidistance of approximately 5-15 mm. In other embodiments, each mark 209 may be spaced equidistance of approximately 10 mm.

Referring to FIGS. 20-24, the tube breaker 200 has a plurality of recesses 219. The plurality of recesses 219 is disposed on the tube breaker 200 along the longitudinal axis 205. Having a plurality of recesses 219 enables a lightweight design as compared with a tube breaker 200 absent recesses and provides advantages to the operator such that the operator can grip the tube breaker 200 more firmly and securely since the plurality of recesses 219 and the arrangement of thereof operates to hold out against sliding of the gripping hand when employing an action of breaking.

Referring to FIGS. 20-24, the side 203 of the protuberance portion 201 is a generally curved concave surface. The generally curved concave surface provides advantages to the operator such that the operator can grip the protuberance more conveniently and firmly as compared with the side 203 absent it when employing an action of breaking. It should be appreciated that other shapes may be employed.

Referring to FIGS. 20-24, the upper portion 211 is chamfered at the first end 212 such that the cross-sectional areas 213 are decreasing along the longitudinal axis 205 toward the first end 212. The lower portion 215 is also chamfered at the second end 216 such that the cross-sectional areas 217 are decreasing along the longitudinal axis 205 toward the first end 216. It should be appreciated that other shapes may be employed.

In some embodiments, the inside of the tube breaker 200 may be hollow or solid, or a combination thereof.

In some embodiments, a tube breaker may be made of a monolithic piece of material. In other embodiments, a tube breaker may be constructed from one or more segments that are assembled together.

In some embodiments, a tube breaker may be comprised of titanium, stainless steel, polymer, or a combination thereof.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

As used herein, the singular forms "a," "an," and "the" are intended to include the plural forms as well, unless the context clearly indicates otherwise. The term "proximal" as used in connection with any object refers to the portion of the object that is closest to the operator of the object (or some other stated reference point), and the term "distal" refers to the portion of the object that is farthest from the operator of the object (or some other stated reference point). The term "operator" means and refers to any professional or paraprofessional who delivers clinical care to a medical patient, particularly in connection with the delivery of care.

Anatomical references as used herein are intended to have the standard meaning for such terms as understood in the medical community. For example, the application may include reference to the following terms: "cephalad," "cranial" and "superior" indicate a direction toward the head, and the terms "caudad" and "inferior" indicate a direction toward the feet. Likewise, the terms "dorsal" and "posterior" indicate a direction toward the back, and the terms "ventral" and "anterior" indicate a direction toward the front. And the term "lateral" indicates a direction toward a side of the patient. The term "medial" indicates a direction toward the midline of the patient, and away from the side, the term "ipsalateral" indicates a direction toward a side that is proximal to the operator, or the object being referenced, and the term "contralateral" indicates a direction toward a side that is distal to the operator, or the object being referenced. And, more specifically with respect to the directional movement of an implant according to the methods of the disclosure, sideways refers to the general direction of movement within the disc space between the endplates from the position of the inserted instruments toward one or the other of the contralateral and ipsilateral portions of the disc space. In the case of a TLIF procedure, such sideways motion will generally be in a medial direction relative to the disc space. Though in other types of surgical access, particularly within the spine, sideways movement may be either medial or lateral relative to the disc space, and in other surgical contexts sideways is away from the initial position of the implant. Further, with respect to the movement of an implant by action of the surgical instruments, the movement may also be rotational, wherein the action of the instruments directs the implant sideways and also in a rotational or pivotal motion. More generally, any and all terms providing spatial references to anatomical features shall have meaning that is customary in the art.

Unless otherwise indicated, all numbers expressing quantities, properties, and so forth as used in the specification, drawings and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

References to visualization using radiography as may be described in the exemplary techniques herein are merely representative of the options for the operator to visualize the surgical field and the patient in one of many available modalities. It will be understood by one of ordinary skill in the art that alternate devices and alternate modalities of visualization may be employed depending on the availability in the operating room, the preferences of the operator and other factors relating to exposure limits. While confirmation of instrument placement in the course of the technique is appropriate, the frequency and timing relative to the sequence of steps in the technique may be varied and the description herein is not intended to be limiting. Accordingly, more, or fewer images, from more or fewer perspectives, may be collected.

One of ordinary skill will appreciate that references to positions in the body are merely representative for a particular surgical approach. Further, all references herein are made in the context of the representative images shown in the drawings. Fewer or additional instruments, including generic instruments, may be used according to the preference of the operator. Moreover, references herein to specific instruments are not intended to be limiting in terms of the options for use of other instruments where generic options are available, or according to the preference of the operator.

While the disclosed embodiments have been described and depicted in the drawings in the context of the human spine, it should be understood by one of ordinary skill that all or various aspects of the embodiments hereof may be used in in connection with other species and within any species on other parts of the body where deep access within the tissue is desirable.

While various inventive aspects, concepts and features of the general inventive concepts are described and illustrated herein in the context of various exemplary embodiments, these various aspects, concepts, and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts and features into additional embodiments and uses within the scope of the general inventive concepts, even if such embodiments are not expressly disclosed herein. Additionally, even though some features, concepts and aspects of the inventions may be described herein as being a preferred arrangement or method, such description is not intended to suggest that such feature is required or necessary unless expressly so stated. Still further, exemplary, or representative values and ranges may be included to assist in understanding the present disclosure; however, such values and ranges are not to be construed in a limiting sense and are intended to be critical values or ranges only if so expressly stated.

Embodiments of the invention also include:

In some embodiments, provided is a length adjustable tubular retractor comprising a cylindrical body and at least one groove.

According to such embodiments, the cylindrical body has a proximal end, distal end, internal surface, and exterior surface, the internal surface faces toward a central axis of the cylindrical body, and the exterior surface faces away from the central axis of the cylindrical body.

According to such embodiments, the at least one groove is circumferentially disposed along the exterior surface of the cylindrical body between the proximal end and the distal end and is disposed at a predetermined position along the central axis from the proximal end to the distal end. The at least one groove is configured such that the cylindrical body is breakable at each of the predetermined positions to form a size-selected length adjustable tubular retractor.

In some embodiments, each predetermined position is spaced equidistance of approximately 5-15 mm.

In some embodiments, each predetermined position is spaced equidistance of approximately 10 mm.

In some embodiments, the at least one groove includes a V-shape, the V-shape having an angle at its apex along the exterior surface.

In some embodiments, the angle is between about 15° and about 115°.

In some embodiments, the angle is about 65°.

In some embodiments, the at least one groove includes a U-shape, the U-shape having a curvature along the exterior surface.

In some embodiments, the length adjustable tubular retractor further includes at least one interior groove disposed circumferentially along the internal surface of the cylindrical body between the proximal end and the distal end, and the at least one interior groove is disposed at a predetermined position along the central axis from the proximal end to the distal end.

In some embodiments, the cylindrical body is breakable at each predetermined position.

In some embodiments, the cylindrical body is comprised of titanium, stainless steel, polymer, or a combination thereof.

In some embodiments, the length adjustable tubular retractor further includes a retractor arm extending from the proximal end of the cylindrical body.

In some embodiments, the length adjustable tubular retractor further includes a retractor handle, the retractor handle comprising a ring configured to be attached to the length adjustable tubular retractor, the ring formed directly onto the length adjustable tubular retractor such that the ring is fixedly attached to the length adjustable tubular retractor, and an arm extending from the ring.

In some embodiments, the retractor handle is comprised of titanium, stainless steel, polymer, or a combination thereof.

In some embodiments, the retractor handle is disposed such that the proximal end of the cylindrical body protrudes from the retractor handle.

In some embodiments, the length adjustable tubular retractor further includes the retractor handle and a frame extending from the retractor handle, the frame having two generally planar arms, the two generally planar arms facing one another, the two generally planar arms configured to be attached to a table arm. The frame is configured to receive a cylindrical fastening device such that the cylindrical fastening device clamps the frame and fixes the length adjustable tubular retractor thereby when the cylindrical fastening device engages in a fastening mode.

In some embodiments, provided is a length adjustable tubular retractor comprising a cylindrical body, at least one groove, and at least one through slot.

According to such embodiments, the cylindrical body has a proximal end, distal end, internal surface, and exterior surface, the internal surface faces toward a central axis of the cylindrical body, and the exterior surface faces away from the central axis of the cylindrical body.

According to such embodiments, the at least one groove is circumferentially disposed along the exterior surface of the cylindrical body between the proximal end and the distal end and is disposed at a predetermined position along the central axis from the proximal end to the distal end. The at least one groove is configured such that the cylindrical body is breakable at each of the predetermined positions to form a size-selected length adjustable tubular retractor.

According to such embodiments, the at least one through slot is circumferentially disposed along the cylindrical body between the proximal end and the distal end, and the at least one through slot is disposed at a predetermined position along the central axis. The at least one through slot is configured such that the cylindrical body is disconnected along and at the at least one through slot and breakable at each of the predetermined positions to form a size-selected length adjustable tubular retractor.

In some embodiments, each predetermined position is spaced equidistance of approximately 5-15 mm.

In some embodiments, each predetermined position is spaced equidistance of approximately 10 mm.

In some embodiments, each predetermined position includes a groove and a through slot.

In some embodiments, the at least one groove includes a V-shape, the V-shape having an angle at its apex along the exterior surface.

In some embodiments, the angle is between about 15° and about 115°.

In some embodiments, the angle is about 65°.

In some embodiments, the at least one groove includes a U-shape, the U-shape having a curvature along the exterior surface.

In some embodiments, the length adjustable tubular retractor further includes at least one interior groove disposed circumferentially along the internal surface of the cylindrical body between the proximal end and the distal end, and the at least one interior groove is disposed at a predetermined position along the central axis from the proximal end to the distal end.

In some embodiments, each predetermined position includes a groove, a through slot, and an interior groove.

In some embodiments, the at least one through slot is a plurality of through slots, the plurality of through slots disposed at a predetermined position differently than the other through slots such that the plurality of through slots disposed at a predetermined position in a staggered arrangement along the central axis.

In some embodiments, the at least one through slot is a plurality of through slots, the plurality of through slots disposed at a predetermined position differently than the other through slots such that the plurality of through slots disposed at a predetermined position in a spiral arrangement along the central axis.

In some embodiments, the plurality of through slots is disposed along the cylindrical body from the distal end toward the proximal end at each predetermined position such that the plurality of through slots disposed at a predetermined position in a spiral arrangement along the central axis, and a following through slot is arranged to rotate an angle about the central axis.

In some embodiments, the angle is 30°

In some embodiments, the number of the plurality of through slots is six.

In some embodiments, the cylindrical body is breakable at each of the predetermined positions.

In some embodiments, the cylindrical body is comprised of titanium, stainless steel, polymer, or a combination thereof.

In some embodiments, each predetermined position includes a plurality of through slots.

In some embodiments, the length adjustable tubular retractor further includes a retractor arm extending from the proximal end of the cylindrical body.

In some embodiments, the length adjustable tubular retractor further includes a retractor handle, the retractor handle comprising a ring configured to be attached to the length adjustable tubular retractor, the ring formed directly onto the length adjustable tubular retractor such that the ring is fixedly attached to the length adjustable tubular retractor, and an arm extending from the ring.

In some embodiments, the retractor handle is comprised of titanium, stainless steel, polymer, or a combination thereof.

In some embodiments, the retractor handle is disposed such that the proximal end of the cylindrical body protrudes from the retractor handle.

In some embodiments, the length adjustable tubular retractor further includes the retractor handle and a frame extending from the retractor handle, the frame having two generally planar arms, the two generally planar arms facing one another, the two generally planar arms configured to be attached to a table arm. The frame is configured to receive a cylindrical fastening device such that the cylindrical fastening device clamps the frame and fixes the length adjustable tubular retractor thereby when the cylindrical fastening device engages in a fastening mode.

In some embodiments, provided is a length adjustable tubular retractor including a cylindrical body having a hollow interior, a central axis, proximal and distal ends, and internal and exterior surfaces, where one or both of the internal surface and the exterior surfaces of the cylindrical body includes at least one or a plurality of grooves or through slots or a combination thereof circumferentially disposed along the cylindrical body, each one of the at least one or a plurality of grooves or through slots or a combination thereof located at a predetermined position along the cylindrical body, each one of the at least one or plurality of the grooves, through slots or combination thereof positioned along the cylindrical body between the proximal end and the distal end, According to such embodiments, each of the at least one or a plurality of grooves, through slots or a combination thereof is configured such that the cylindrical body is breakable at each of the predetermined positions to form a size-selected length adjustable tubular. The retractor is one of disposable or reusable.

In some embodiments, provided is a length adjustable tubular retractor including a cylindrical body, at least one groove, at least one through slot, and at least one interior groove.

According to such embodiments, the cylindrical body has a proximal end, distal end, internal surface, and exterior surface, the internal surface faces toward a central axis of the cylindrical body, and the exterior surface faces away from the central axis of the cylindrical body.

According to such embodiments, the at least one groove circumferentially is disposed along the exterior surface of the cylindrical body between the proximal end and the distal end, and the at least one groove is disposed at a predetermined position along the central axis from the proximal end to the distal end. The at least one groove is configured such that the cylindrical body is breakable at each of the predetermined positions to form a size-selected length adjustable tubular retractor.

According to such embodiments, the at least one through slot circumferentially is disposed along the cylindrical body between the proximal end and the distal end, and the at least one through slot is disposed at a predetermined position along the central axis. The at least one through slot is configured such that the cylindrical body is disconnected along and at the at least one through slot and breakable at each of the predetermined positions to form a size-selected length adjustable tubular retractor.

According to such embodiments, the at least one interior groove is disposed circumferentially along the internal surface of the cylindrical body between the proximal end and the distal end, and the at least one interior groove is disposed at a predetermined position along the central axis from the proximal end to the distal end.

According to such embodiments, each predetermined position includes a groove, an interior groove, and a through slot, and the cylindrical body is breakable at each of the predetermined positions.

In some embodiments, provided is a surgical system comprising a length adjustable tubular retractor including a cylindrical body and at least one groove and a retractor handle.

According to such embodiments, the cylindrical body has a proximal end, distal end, internal surface, and exterior surface, the internal surface faces toward a central axis of the cylindrical body, and the exterior surface faces away from the central axis of the cylindrical body. The at least one groove is circumferentially disposed along the exterior surface of the cylindrical body between the proximal end and the distal end and is disposed at a predetermined position along the central axis from the proximal end to the distal end. The at least one groove is configured such that the cylindrical body is breakable at each of the predetermined positions to form a size-selected length adjustable tubular retractor.

According to such embodiments, the retractor handle includes a ring, an arm, and a mounting bracket. The ring is configured to be attached to the length adjustable tubular retractor, and the ring is formed directly onto the length adjustable tubular retractor such that the ring is fixedly attached to the tubular retractor. The arm extends from the ring. The mounting bracket includes a plate, first and second arms, and at least one device emplacement. The at least one device emplacement is disposed adjacent to the plate to receive and hold in-place a surgical tool at a fixed position and orientation.

In some embodiments, the surgical system further includes a frame extending from the retractor handle, the frame having two generally planar arms, the two generally planar arms facing one another, the two generally planar arms configured to be attached to a table arm. The frame is configured to receive a cylindrical fastening device such that the cylindrical fastening device clamps the frame and fixes the length adjustable tubular retractor thereby when the cylindrical fastening device engages in a fastening mode.

In some embodiments, the surgical system further includes a tube breaker for adjusting the length of a length adjustable tubular retractor including a protuberance portion, an upper portion, a lower portion, and a plurality of marks.

According to such embodiments, the protuberance portion has a top, side, and bottom, the side of the protuberance portion is disposed between the top and bottom of the protuberance portion, the protuberance portion extends from the top toward the bottom along a longitudinal axis, and the protuberance portion has cross-sectional areas along the longitudinal axis.

According to such embodiments, the upper portion has a generally cylindrical shape, the upper portion is adapted to be slidably inserted in a length adjustable tubular retractor, the upper portion has a first end, the upper portion extends from the first end along the longitudinal axis toward the protuberance portion and connects to the top of the protuberance portion, and the upper portion has cross-sectional areas along the longitudinal axis. The cross-sectional area at the top of the protuberance portion is greater than the cross-sectional area of the upper portion where the upper portion connects to the top of the protuberance.

According to such embodiments, the lower portion has a generally cylindrical shape, the lower portion is adapted to be slidably inserted in a length adjustable tubular retractor, the lower portion has a second end, the lower portion extends from the second end along the longitudinal axis toward the protuberance portion and connects to the bottom of the protuberance portion, and the lower portion has cross-sectional areas along the longitudinal axis. The cross-sectional area at the bottom of the protuberance portion is greater than the cross-sectional area of the lower portion where the lower portion connects to the bottom of the protuberance portion.

According to such embodiments, the plurality of marks is disposed on the upper portion, protuberance portion, and lower portion, and each mark indicates a relative longitudinal location measured from the first end.

According to such embodiments, the upper portion and lower portion are configured to enable a break, when inserted in a length adjustable tubular retractor, at a selected predetermined position on the length adjustable tubular retractor by an action of breaking. The action of breaking is accomplished by hands of the operator gripping the length adjustable tubular retractor and tube breaker and applying force or moment to induce bending moment greater than the bending moment the selected predetermined position on the length adjustable tubular retractor can withstand.

In some embodiments, provided is a surgical system comprising a length adjustable tubular retractor including a cylindrical body, at least one groove, and at least one through slot and a retractor handle.

According to such embodiments, the cylindrical body has a proximal end, distal end, internal surface, and exterior surface, the internal surface faces toward a central axis of the cylindrical body, and the exterior surface faces away from the central axis of the cylindrical body. The at least one groove is circumferentially disposed along the exterior surface of the cylindrical body between the proximal end and the distal end and is disposed at a predetermined position along the central axis from the proximal end to the distal end. The at least one groove is configured such that the cylindrical body is breakable at each of the predetermined positions to form a size-selected length adjustable tubular retractor. The at least one through slot is circumferentially disposed along the cylindrical body between the proximal end and the distal end, and the at least one through slot is disposed at a predetermined position along the central axis. The at least one through slot is configured such that the cylindrical body is disconnected along and at the at least one through slot and breakable at each of the predetermined positions to form a size-selected length adjustable tubular retractor.

According to such embodiments, the retractor handle includes a ring, an arm, and a mounting bracket. The ring is configured to be attached to the length adjustable tubular retractor, and the ring is formed directly onto the length adjustable tubular retractor such that the ring is fixedly attached to the tubular retractor. The arm extends from the ring. The mounting bracket includes a plate, first and second arms, and at least one device emplacement. The at least one device emplacement is disposed adjacent to the plate to receive and hold in-place a surgical tool at a fixed position and orientation.

In some embodiments, the surgical system further includes a frame extending from the retractor handle, the frame having two generally planar arms, the two generally planar arms facing one another, the two generally planar arms configured to be attached to a table arm. The frame is configured to receive a cylindrical fastening device such that the cylindrical fastening device clamps the frame and fixes the length adjustable tubular retractor thereby when the cylindrical fastening device engages in a fastening mode.

In some embodiments, the surgical system further includes a tube breaker for adjusting the length of a length adjustable tubular retractor including a protuberance portion, an upper portion, a lower portion, and a plurality of marks.

According to such embodiments, the protuberance portion has a top, side, and bottom, the side of the protuberance portion is disposed between the top and bottom of the protuberance portion, the protuberance portion extends from the top toward the bottom along a longitudinal axis, and the protuberance portion has cross-sectional areas along the longitudinal axis.

According to such embodiments, the upper portion has a generally cylindrical shape, the upper portion is adapted to be slidably inserted in a length adjustable tubular retractor, the upper portion has a first end, the upper portion extends from the first end along the longitudinal axis toward the protuberance portion and connects to the top of the protuberance portion, and the upper portion has cross-sectional areas along the longitudinal axis. The cross-sectional area at the top of the protuberance portion is greater than the cross-sectional area of the upper portion where the upper portion connects to the top of the protuberance.

According to such embodiments, the lower portion has a generally cylindrical shape, the lower portion is adapted to be slidably inserted in a length adjustable tubular retractor, the lower portion has a second end, the lower portion extends from the second end along the longitudinal axis toward the protuberance portion and connects to the bottom of the protuberance portion, and the lower portion has cross-sectional areas along the longitudinal axis. The cross-sectional area at the bottom of the protuberance portion is greater than the cross-sectional area of the lower portion where the lower portion connects to the bottom of the protuberance portion.

According to such embodiments, the plurality of marks is disposed on the upper portion, protuberance portion, and lower portion, and each mark indicates a relative longitudinal location measured from the first end.

According to such embodiments, the upper portion and lower portion are configured to enable a break, when inserted in a length adjustable tubular retractor, at a selected predetermined position on the length adjustable tubular retractor by an action of breaking. The action of breaking is accomplished by hands of the operator gripping the length adjustable tubular retractor and tube breaker and applying force or moment to induce bending moment greater than the bending moment the selected predetermined position on the length adjustable tubular retractor can withstand.

Yet, in other embodiments, the tool can be an apparatus, a tube breaker. A tube breaker is used to enable a break of a length adjustable tubular retractor according to any one of a variety of embodiments as described above and herein at a selected predetermined position.

In some embodiments, provided is a tube breaker for adjusting the length of a length adjustable tubular retractor comprising a protuberance portion, an upper portion, a lower portion, and a plurality of marks.

According to such embodiments, the protuberance portion has a top, side, and bottom, the side of the protuberance portion is disposed between the top and bottom of the protuberance portion, the protuberance portion extends from the top toward the bottom along a longitudinal axis, and the protuberance portion has cross-sectional areas along the longitudinal axis.

According to such embodiments, the upper portion has a generally cylindrical shape, the upper portion is adapted to be slidably inserted in a length adjustable tubular retractor, the upper portion has a first end, the upper portion extends from the first end along the longitudinal axis toward the protuberance portion and connects to the top of the protuberance portion, and the upper portion has cross-sectional areas along the longitudinal axis. The cross-sectional area at the top of the protuberance portion is greater than the cross-sectional area of the upper portion where the upper portion connects to the top of the protuberance.

According to such embodiments, the lower portion has a generally cylindrical shape, the lower portion is adapted to be slidably inserted in a length adjustable tubular retractor, the lower portion has a second end, the lower portion extends from the second end along the longitudinal axis toward the protuberance portion and connects to the bottom of the protuberance portion, and the lower portion has cross-sectional areas along the longitudinal axis. The cross-sectional area at the bottom of the protuberance portion is greater than the cross-sectional area of the lower portion where the lower portion connects to the bottom of the protuberance portion.

According to such embodiments, the plurality of marks is disposed on the upper portion, protuberance portion, and lower portion, and each mark indicates a relative longitudinal location measured from the first end.

According to such embodiments, the upper portion and lower portion are configured to enable a break, when inserted in a length adjustable tubular retractor, at a selected predetermined position on the length adjustable tubular retractor by an action of breaking. The action of breaking is accomplished by hands of the operator gripping the length adjustable tubular retractor and tube breaker and applying force or moment to induce bending moment greater than the bending moment the selected predetermined position on the length adjustable tubular retractor can withstand.

In some embodiments, the upper portion is chamfered at the first end such that the cross-sectional areas are decreasing along the longitudinal axis toward the first end.

In some embodiments, the lower portion is chamfered at the second end such that the cross-sectional areas are decreasing along the longitudinal axis toward the second end.

In some embodiments, each mark is spaced equidistance of approximately 5-15 mm.

In some embodiments, each mark is spaced equidistance of approximately 10 mm.

In some embodiments, the tube breaker further includes a plurality of recesses.

In some embodiments, the plurality of recesses is disposed along the longitudinal axis on the tube breaker, each recess having at least one complementary recess disposed on the same plane perpendicular to the longitudinal axis.

In some embodiments, the side of the protuberance portion includes a generally concave curved surface.

In some embodiments, the tube breaker is made of a monolithic piece of material.

In some embodiments, the tube breaker is constructed from one or more segments that are assembled together.

In some embodiments, the tube breaker is comprised of titanium, stainless steel, polymer, or a combination thereof.

Also provided is a method for providing a size-selected length adjustable tubular retractor. The method includes providing a length adjustable tubular retractor according to any one of a variety of embodiments as described above and herein, selecting one of the predetermined positions along the cylindrical body at which to break the retractor, and engaging a tool to enable a break at the selected predetermined position at the groove, through slot or combination thereof located at the selected predetermined position.

In some embodiments of the method, the tool is a pair of human hands, one hand disposed proximal to the selected predetermined position and the other hand disposed distal to the selected predetermined position, each hand gripping the retractor along the central axis, and the action of breaking is accomplished by rotation of the hands off of the central axis to break the cylindrical body.

In some embodiments of the method, the tool is a pair of opposable insertion rods, clamps, or a combination thereof, one of which is engaged with the cylindrical body disposed proximal to the selected predetermined position and the other of which is engaged with the cylindrical body distal to the selected predetermined position, each of the pair of opposable insertion rods, clamps, or a combination thereof engaging the retractor along the central axis, and the action of breaking is accomplished by rotation of the pair of opposable insertion rods, clamps, or a combination thereof off of the central axis to break the cylindrical body.

In other embodiments of the method, other tools may be employed to enable breaking or cutting the cylindrical body to provide a size-selected length adjustable tubular retractor.

In an embodiment, the invention provides a length adjustable tubular retractor, including a cylindrical body and at least one groove. The cylindrical body has a proximal end, distal end, internal surface, and exterior surface, the internal surface facing toward a central axis of the cylindrical body, the exterior surface facing away from the central axis of the cylindrical body. The at least one groove is circumferentially disposed along the exterior surface of the cylindrical body between the proximal end and the distal end and is disposed at a predetermined position along the central axis from the proximal end to the distal end. The at least one groove is configured such that the cylindrical body is breakable at each of the predetermined positions to form a size-selected length adjustable tubular retractor.

In some embodiments, each predetermined position is spaced equidistance of approximately 5-15 mm.

In some embodiments, each predetermined position is spaced equidistance of approximately 10 mm.

In some embodiments, the at least one groove includes a V-shape, the V-shape having an angle at its apex along the exterior surface. In some embodiments, the angle is between about 15° and about 115°. Yet, in some embodiments, the angle is about 65°.

In some embodiments, the at least one groove includes a U-shape, the U-shape having a curvature along the exterior surface.

In some embodiments, the length adjustable tubular retractor further includes at least one interior groove disposed circumferentially along the internal surface of the cylindrical body between the proximal end and the distal end, the at least one interior groove disposed at a predetermined position along the central axis from the proximal end to the distal end.

In some embodiments, the cylindrical body is breakable at each predetermined position.

In some embodiments, the cylindrical body is comprised of titanium, stainless steel, polymer, or a combination thereof.

In some embodiments, the length adjustable tubular retractor further includes a retractor arm extending from the proximal end of the cylindrical body.

In some embodiments, the length adjustable tubular retractor further includes a retractor handle, the retractor handle comprising a ring configured to be attached to the length adjustable tubular retractor, the ring formed directly onto the length adjustable tubular retractor such that the ring is fixedly attached to the length adjustable tubular retractor, and an arm extending from the ring. In some embodiments, the retractor handle is comprised of titanium, stainless steel, polymer, or a combination thereof. In some embodiments, the retractor handle is disposed such that the proximal end of the cylindrical body protrudes from the retractor handle. In some embodiments, the length adjustable tubular retractor further includes a frame extending from the retractor handle, the frame having two generally planar arms, the two generally planar arms facing one another, the two generally planar arms configured to be attached to a table arm. The frame is configured to receive a cylindrical fastening device such that the cylindrical fastening device clamps the frame and fixes the length adjustable tubular retractor thereby when the cylindrical fastening device engages in a fastening mode.

In an embodiment, the invention provides a length adjustable tubular retractor, including a cylindrical body, at least one groove, and at least one through slot. The cylindrical body has a proximal end, distal end, internal surface, and exterior surface, the internal surface facing toward a central axis of the cylindrical body, the exterior surface facing away from the central axis of the cylindrical body. The at least one groove is circumferentially disposed along the exterior surface of the cylindrical body between the proximal end and the distal end and is disposed at a predetermined position along the central axis from the proximal end to the distal end. The at least one groove is configured such that the cylindrical body is breakable at each of the predetermined positions to form a size-selected length adjustable tubular retractor. The at least one through slot is circumferentially disposed along the cylindrical body between the proximal end and the distal end and is disposed at a predetermined position along the central axis. The at least one through slot is configured such that the cylindrical body is disconnected along and at the at least one through slot and breakable at each of the predetermined positions to form a size-selected length adjustable tubular retractor.

In some embodiments, each predetermined position is spaced equidistance of approximately 5-15 mm.

In some embodiments, each predetermined position is spaced equidistance of approximately 10 mm.

In some embodiments, each predetermined position includes a groove and a through slot. In some embodiments, the through slot includes a plurality of through slots. In some embodiments, the plurality of through slots is disposed at a predetermined position differently than the other through slots such that the plurality of through slots disposed at a predetermined position in a staggered arrangement along the central axis. In some embodiments, the plurality of through slots is disposed at a predetermined position differently than the other through slots such that the plurality of through slots is disposed at a predetermined position in a spiral arrangement along the central axis. In some embodiments, the plurality of through slots is disposed along the cylindrical body from the distal end toward the proximal end at each predetermined position such that a following through slot is arranged to rotate an angle about the central axis. In some embodiments, the angle is 30°. In some embodiments, the number of the plurality of through slots is six.

In some embodiments, the at least one groove includes a V-shape, the V-shape having an angle at its apex along the exterior surface. In some embodiments, the angle is between about 15° and about 115°. In some embodiments, the angle is about 65°.

In some embodiments, the at least one groove includes a U-shape, the U-shape having a curvature along the exterior surface.

In some embodiments, the length adjustable tubular retractor further includes at least one interior groove disposed circumferentially along the internal surface of the cylindrical body between the proximal end and the distal end, the at least one interior groove disposed at a predetermined position along the central axis from the proximal end to the distal end.

In some embodiments, the cylindrical body is breakable at each of the predetermined positions.

In some embodiments, the cylindrical body is comprised of titanium, stainless steel, polymer, or a combination thereof.

In some embodiments, each predetermined position includes a plurality of through slots.

In some embodiments, the length adjustable tubular retractor further includes a retractor arm extending from the proximal end of the cylindrical body.

In some embodiments, the length adjustable tubular retractor further includes a retractor handle. The retractor handle includes a ring configured to be attached to the length adjustable tubular retractor, the ring formed directly onto the length adjustable tubular retractor such that the ring is fixedly attached to the length adjustable tubular retractor, and an arm extending from the ring. In some embodiments, the retractor handle is comprised of titanium, stainless steel, polymer, or a combination thereof. In some embodiments, the retractor handle is disposed such that the proximal end of the cylindrical body protrudes from the retractor handle.

In some embodiments, the length adjustable tubular retractor includes the retractor handle and a frame. The frame extends from the retractor handle and has two generally planar arms, the two generally planar arms facing one another, the two generally planar arms configured to be attached to a table arm. The frame is configured to receive a cylindrical fastening device such that the cylindrical fastening device clamps the frame and fixes the length adjustable tubular retractor thereby when the cylindrical fastening device engages in a fastening mode.

In an embodiment, the invention provides a surgical system that includes a length adjustable tubular retractor and a retractor handle. The retractor handle includes: a ring configured to be attached to the length adjustable tubular retractor, the ring formed directly onto the length adjustable tubular retractor such that the ring is fixedly attached to the tubular retractor; an arm extending from the ring; and a mounting bracket, including: a plate; first and second arms adjacent to and extending from the plate; and at least one device emplacement disposed adjacent to the plate to receive and hold in-place a surgical tool at a fixed position and orientation. The length adjustable tubular retractor includes a cylindrical body and at least one groove. The cylindrical body has a proximal end, distal end, internal surface, and exterior surface, the internal surface facing toward a central axis of the cylindrical body, the exterior surface facing away from the central axis of the cylindrical body. The at least one groove is circumferentially disposed along the exterior surface of the cylindrical body between the proximal end and the distal end and is disposed at a predetermined position along the central axis from the proximal end to the distal end. The at least one groove is configured such that the cylindrical body is breakable at each of the predetermined positions to form a size-selected length adjustable tubular retractor.

In some embodiments, the surgical system further includes a frame extending from the retractor handle, the frame having two generally planar arms, the two generally planar arms facing one another, the two generally planar arms configured to be attached to a table arm. The frame is configured to receive a cylindrical fastening device such that the cylindrical fastening device clamps the frame and fixes the length adjustable tubular retractor thereby when the cylindrical fastening device engages in a fastening mode.

In an embodiment, the invention provides a surgical system includes a length adjustable tubular retractor and a retractor handle. The retractor handle includes: a ring configured to be attached to the length adjustable tubular retractor, the ring formed directly onto the length adjustable tubular retractor such that the ring is fixedly attached to the tubular retractor; an arm extending from the ring; and a mounting bracket, including: a plate; first and second arms adjacent to and extending from the plate; and at least one device emplacement disposed adjacent to the plate to receive and hold in-place a surgical tool at a fixed position and orientation. The length adjustable tubular retractor includes a cylindrical body, at least one groove, and at least one through slot. The cylindrical body has a proximal end, distal end, internal surface, and exterior surface, the internal surface facing toward a central axis of the cylindrical body, the exterior surface facing away from the central axis of the cylindrical body. The at least one groove is circumferentially disposed along the exterior surface of the cylindrical body between the proximal end and the distal end and is disposed at a predetermined position along the central axis from the proximal end to the distal end. The at least one groove is configured such that the cylindrical body is breakable at each of the predetermined positions to form a size-selected length adjustable tubular retractor. The at least one through slot is circumferentially disposed along the cylindrical body between the proximal end and the distal end and is disposed at a predetermined position along the central axis. The at least one through slot is configured such that the cylindrical body is disconnected along and at the at least one through slot and breakable at each of the predetermined positions to form a size-selected length adjustable tubular retractor.

In some embodiments, the surgical system further includes a frame extending from the retractor handle, the frame having two generally planar arms, the two generally planar arms facing one another, the two generally planar arms configured to be attached to a table arm. The frame is configured to receive a cylindrical fastening device such that the cylindrical fastening device clamps the frame and fixes the length adjustable tubular retractor thereby when the cylindrical fastening device engages in a fastening mode.

In an embodiment, the invention provides a length adjustable tubular retractor. The retractor includes a cylindrical body having a hollow interior, a central axis, proximal and distal ends, and internal and exterior surfaces, where one or both of the internal surface and the exterior surfaces of the cylindrical body includes at least one or a plurality of grooves or through slots or a combination thereof circumferentially disposed along the cylindrical body, each one of the at least one or a plurality of grooves or through slots or a combination thereof located at a predetermined position along the cylindrical body, each one of the at least one or plurality of the grooves, through slots or combination thereof positioned along the cylindrical body between the proximal end and the distal end. Each of the at least one or a plurality of grooves, through slots or a combination thereof is configured such that the cylindrical body is breakable at each of the predetermined positions to form a size-selected length adjustable tubular. The retractor is one of disposable or reusable.

In an embodiment, the invention provides a method for providing a size-selected length adjustable tubular retractor. The method includes (i) providing a length adjustable tubular retractor; (ii) selecting one of the predetermined positions along the cylindrical body at which to break the retractor; and (iii) engaging a tool to enable a break at the selected predetermined position at the groove, through slot or combination thereof located at the selected predetermined position. The length adjustable tubular retractor includes a cylindrical body having a hollow interior, a central axis, proximal and distal ends, and internal and exterior surfaces, where one or both of the internal surface and the exterior surfaces of the cylindrical body includes at least one or a plurality of grooves or through slots or a combination thereof circumferentially disposed along the cylindrical body, each one of the at least one or a plurality of grooves or through slots or a combination thereof located at a predetermined position along the cylindrical body, each one of the at least one or plurality of the grooves, through slots or combination thereof positioned along the cylindrical body between the proximal end and the distal end. Each of the at least one or a plurality of grooves, through slots or a combination thereof is configured such that the cylindrical body is breakable at each of the predetermined positions to form a size-selected length adjustable tubular. The retractor is one of disposable or reusable.

In some embodiments, the tool is a pair of human hands, one hand disposed proximal to the selected predetermined position and the other hand disposed distal to the selected predetermined position, each hand gripping the retractor along the central axis. The action of breaking is accomplished by rotation of the hands off of the central axis to break the cylindrical body.

In some embodiments, the tool is a pair of opposable insertion rods, clamps, or a combination thereof, one of which is engaged with the cylindrical body disposed proximal to the selected predetermined position and the other of which is engaged with the cylindrical body distal to the selected predetermined position, each of the pair of opposable insertion rods, clamps, or a combination thereof engaging the retractor along the central axis. The action of breaking is accomplished by rotation of the pair of opposable insertion rods, clamps, or a combination thereof off of the central axis to break the cylindrical body.

In an embodiment, the invention provides a tube breaker for adjusting the length of a length adjustable tubular retractor. The tube breaker includes a protuberance portion, an upper portion, a lower portion, and a plurality of marks. The protuberance portion has a top, side, and bottom, the side of the protuberance portion is disposed between the top and bottom of the protuberance portion, the protuberance portion extends from the top toward the bottom along a longitudinal axis, and the protuberance portion has cross-sectional areas along the longitudinal axis. The upper portion has a generally cylindrical shape, the upper portion is adapted to be slidably inserted in a length adjustable tubular retractor, the upper portion has a first end, the upper portion extends from the first end along the longitudinal axis toward the protuberance portion and connects to the top of the protuberance portion, and the upper portion has cross-sectional areas along the longitudinal axis. The cross-sectional area at the top of the protuberance portion is greater than the cross-sectional area of the upper portion where the upper portion connects to the top of the protuberance. The lower portion has a generally cylindrical shape, the lower portion is adapted to be slidably inserted in a length adjustable tubular retractor, the lower portion has a second end, the lower portion extends from the second end along the longitudinal axis toward the protuberance portion and connects to the bottom of the protuberance portion, and the lower portion has cross-sectional areas along the longitudinal axis. The cross-sectional area at the bottom of the protuberance portion is greater than the cross-sectional area of the lower portion where the lower portion connects to the bottom of the protuberance portion; and a plurality of marks disposed on the upper portion, protuberance portion, and lower portion, each mark indicating a relative longitudinal location measured from the first end. The upper portion and lower portion are configured to enable a break, when inserted in a length adjustable tubular retractor, at a selected predetermined position on the length adjustable tubular retractor by an action of breaking. The action of breaking is accomplished by hands of the operator gripping the length adjustable tubular retractor and tube breaker and applying force or moment to induce bending moment greater than the bending moment the selected predetermined position on the length adjustable tubular retractor can withstand.

In some embodiments, the upper portion is chamfered at the first end such that the cross-sectional areas are decreasing along the longitudinal axis toward the first end.

In some embodiments, the lower portion is chamfered at the second end such that the cross-sectional areas are decreasing along the longitudinal axis toward the second end.

In some embodiments, each mark is spaced equidistance of approximately 5-15 mm.

In some embodiments, each mark is spaced equidistance of approximately 10 mm.

In some embodiments, the tube breaker further includes a plurality of recesses. In some embodiments, the plurality of recesses is disposed along the longitudinal axis on the tube breaker, each recess having at least one complementary recess disposed on the same plane perpendicular to the longitudinal axis.

In some embodiments, the side of the protuberance portion includes a generally concave curved surface.

In some embodiments, the tube breaker is made of a monolithic piece of material.

In some embodiments, the tube breaker is constructed from one or more segments that are assembled together.

In some embodiments, the tube breaker is comprised of titanium, stainless steel, polymer, or a combination thereof.

What is claimed is:

1. A length adjustable tubular retractor, comprising:
a scored tubular retractor comprising a cylindrical body, the scored tubular retractor adapted for breaking away at least a portion of the cylindrical body to thereby adjust the length of the tubular retractor, the cylindrical body having a proximal end, a distal end, an internal surface, and an exterior surface, the internal surface facing toward a central axis of the cylindrical body, the exterior surface facing away from the central axis of the cylindrical body, the cylindrical body comprising at least one exterior groove disposed circumferentially within the exterior surface of the cylindrical body and positioned between the proximal end and the distal end, and at least one through slot disposed through the exterior and interior surfaces of the cylindrical body and extending circumferentially along a portion of the cylindrical body and aligned with and adjacent the at least one exterior groove.

2. The length adjustable tubular retractor of claim 1, wherein the at least one exterior groove comprises a V-shape, the V-shape having an angle at its apex along the exterior surface.

3. The length adjustable tubular retractor of claim 1, wherein the at least one exterior groove comprises a U-shape, the U-shape having a curvature along the exterior surface.

4. The length adjustable tubular retractor of claim 1, comprising a plurality of aligned exterior grooves and through slots spaced apart along the length of the cylindrical body and positioned between the proximal end and the distal end.

5. The length adjustable tubular retractor of claim 1, wherein the plurality of aligned exterior grooves and through slots is disposed in a staggered arrangement along the length of the cylindrical body and positioned between the proximal end and the distal end.

6. The length adjustable tubular retractor of claim 1, wherein the plurality of aligned exterior grooves and through slots is disposed in a spiral arrangement along the length of the cylindrical body and positioned between the proximal end and the distal end.

7. The length adjustable tubular retractor of claim 1, wherein each of the plurality of aligned exterior grooves and through slots is disposed sequentially along the length of the cylindrical body and positioned between the proximal end and the distal end at 90 degrees from each adjacent through slot.

8. The length adjustable tubular retractor of claim 1, comprising at least one interior groove disposed circumferentially within the internal surface of the cylindrical body, the at least one interior groove aligned with and opposite the at least one exterior groove.

9. The length adjustable tubular retractor of claim 1, comprising a retractor handle extending from the proximal end of the cylindrical body.

10. The length adjustable tubular retractor of claim 9, comprising a frame extending from the retractor handle, the frame having two generally planar arms facing one another and configured to retain one or more attachments extending into the cylindrical body.

11. The length adjustable tubular retractor of claim 10, wherein two generally planar arms facing one another are configured to retain one or more of lighting and suction attachments.

12. A length adjustable tubular retractor, comprising:
a scored tubular retractor comprising a cylindrical body, the scored tubular retractor adapted for breaking away at least a portion of the cylindrical body to thereby adjust the length of the tubular retractor, the cylindrical body having a proximal end, a distal end, an internal surface, and an exterior surface, the internal surface facing toward a central axis of the cylindrical body, the exterior surface facing away from the central axis of the cylindrical body, the cylindrical body comprising at least one exterior groove disposed circumferentially within the exterior surface of the cylindrical body and positioned between the proximal end and the distal end;

at least one through slot disposed through the exterior and interior surfaces of the cylindrical body and extending circumferentially along a portion of the cylindrical body and aligned with and adjacent the at least one exterior groove, wherein each predetermined position comprises an exterior groove and a through slot, and the cylindrical body is breakable at each of the predetermined positions.

13. A method for providing a size-selected length adjustable tubular retractor, comprising:
 a. providing a length adjustable tubular retractor according to claim 1;
 b. selecting one of the predetermined positions along the cylindrical body at which to break the retractor;
 c. engaging a tool to enable a break at the selected predetermined position at the groove located at the selected predetermined position.

14. The method according to claim 13, wherein the tool is a pair of human hands, one hand disposed proximal to the selected predetermined position and the other hand is disposed distal to the selected predetermined position, each hand gripping the retractor along the central axis, and wherein the action of breaking is accomplished by rotation of the hands off of the central axis to break the cylindrical body.

15. A method for providing a size-selected length adjustable tubular retractor, comprising:
 i. providing a length adjustable tubular retractor comprising a scored tubular retractor comprising a cylindrical body, the scored tubular retractor adapted for breaking away at least a portion of the cylindrical body to thereby adjust the length of the tubular retractor, the cylindrical body having a proximal end, a distal end, an internal surface, and an exterior surface, the internal surface facing toward a central axis of the cylindrical body, the exterior surface facing away from the central axis of the cylindrical body, the cylindrical body comprising at least one exterior groove disposed circumferentially within the exterior surface of the cylindrical body and positioned between the proximal end and the distal end;
 ii. selecting one of the predetermined positions along the cylindrical body at which to break the retractor; and
 iii. engaging a tool to enable a break at the selected predetermined position at the groove located at the selected predetermined position,
wherein the tool is a pair of opposable insertion rods, clamps, or a combination thereof, one of which is engaged with the cylindrical body disposed proximal to the selected predetermined position and the other of which is engaged with the cylindrical body distal to the selected predetermined position, each of the pair of opposable insertion rods, clamps, or a combination thereof engaging the retractor along the central axis, and wherein the action of breaking is accomplished by rotation of the pair of opposable insertion rods, clamps, or a combination thereof off of the central axis to break the cylindrical body.

16. A length adjustable tubular retractor system comprising,
 a. a length adjustable tubular retractor comprising a scored tubular retractor comprising a cylindrical body, the scored tubular retractor adapted for breaking away at least a portion of the cylindrical body to thereby adjust the length of the tubular retractor, the cylindrical body having a proximal end, a distal end, an internal surface, and an exterior surface, the internal surface facing toward a central axis of the cylindrical body, the exterior surface facing away from the central axis of the cylindrical body, the cylindrical body comprising at least one exterior groove disposed circumferentially within the exterior surface of the cylindrical body and positioned between the proximal end and the distal end, and
 b. a tube breaker for adjusting the length of the length adjustable tubular retractor, the tube breaker comprising:
 a protuberance portion, the protuberance portion having a top, side, and bottom, the side of the protuberance portion disposed between the top and bottom of the protuberance portion, the protuberance portion extending from the top toward the bottom along a longitudinal axis, the protuberance portion having cross-sectional areas along the longitudinal axis;
 an upper portion, the upper portion having a generally cylindrical shape, the upper portion adapted to be slidably inserted in a length adjustable tubular retractor, the upper portion having a first end, the upper portion extending from the first end along the longitudinal axis toward the protuberance portion and connecting to the top of the protuberance portion, the upper portion having cross-sectional areas along the longitudinal axis, wherein the cross-sectional area at the top of the protuberance portion is greater than the cross-sectional area of the upper portion where the upper portion connects to the top of the protuberance;
 a lower portion, the lower portion having a generally cylindrical shape, the lower portion adapted to be slidably inserted in a length adjustable tubular retractor, the lower portion having a second end, the lower portion extending from the second end along the longitudinal axis toward the protuberance portion and connecting to the bottom of the protuberance portion, the lower portion having cross-sectional areas along the longitudinal axis, wherein the cross-sectional area at the bottom of the protuberance portion is greater than the cross-sectional area of the lower portion where the lower portion connects to the bottom of the protuberance portion; and
 a plurality of marks disposed on the upper portion, protuberance portion, and lower portion, each mark indicating a relative longitudinal location measured from the first end;
 wherein the upper portion and lower portion are configured to enable a break, when inserted in a length adjustable tubular retractor, at a selected predetermined position on the length adjustable tubular retractor by an action of breaking, wherein the action of breaking is accomplished by hands of the operator gripping the length adjustable tubular retractor and tube breaker and applying force or moment to induce bending moment greater than the bending moment the selected predetermined position on the length adjustable tubular retractor can withstand.

17. The length adjustable tubular retractor system of claim 16, comprising a feature selected from the group consisting of (i) the upper portion of the tube breaker is chamfered at the first end such that the cross-sectional areas are decreasing along the longitudinal axis toward the first end, (ii) the lower portion of the tube breaker is chamfered at the second end such that the cross-sectional areas are decreasing along the longitudinal axis toward the second end, (iii) each mark of the tube breaker is spaced equidistance of approximately 5-15 mm, (iv) each mark of the tube breaker is spaced equidistance of approximately 10 mm, (v) and combinations thereof.

18. The length adjustable tubular retractor system according to claim 12, wherein the at least one exterior groove comprises a V-shape, the V-shape having an angle at its apex along the exterior surface.

19. A length adjustable tubular retractor system comprising,
   a. a length adjustable tubular retractor comprising a scored tubular retractor comprising a cylindrical body, the scored tubular retractor adapted for breaking away at least a portion of the cylindrical body to thereby adjust the length of the tubular retractor, the cylindrical body having a proximal end, a distal end, an internal surface, and an exterior surface, the internal surface facing toward a central axis of the cylindrical body, the exterior surface facing away from the central axis of the cylindrical body, the cylindrical body comprising at least one exterior groove disposed circumferentially within the exterior surface of the cylindrical body and positioned between the proximal end and the distal end; and
   b. a tube breaker for adjusting the length of the length adjustable tubular retractor, the tube breaker comprising one of a pair of opposable insertion rods, a pair of clamps, or a combination thereof, one of which pair is engageable with the cylindrical body disposed proximal to the selected predetermined position and the other of which pair is engageable with the cylindrical body distal to the selected predetermined position, each of the pair of opposable insertion rods, the pair of clamps, or combination thereof engaging the retractor along the central axis, and wherein the action of breaking is accomplished by rotation of the pair of opposable insertion rods, the pair of clamps, or combination thereof off of the central axis to break the cylindrical body.

20. The length adjustable tubular retractor system according to claim 18, comprising at least one through slot disposed through and extending circumferentially along a portion of the cylindrical body and aligned with and adjacent the at least one exterior groove.

21. The length adjustable tubular retractor system according to claim 18, wherein the at least one exterior groove comprises a V-shape, the V-shape having an angle at its apex along the exterior surface.

* * * * *